(12) United States Patent
Jarosz et al.

(10) Patent No.: US 11,274,343 B2
(45) Date of Patent: Mar. 15, 2022

(54) METHODS AND COMPOSITIONS FOR TARGETED NUCLEIC ACID SEQUENCE COVERAGE

(71) Applicant: 10X Genomics, Inc., Pleasanton, CA (US)

(72) Inventors: Mirna Jarosz, Mountain View, CA (US); Michael Schnall-Levin, Palo Alto, CA (US)

(73) Assignee: 10X GENOMICS, INC., Pleasanton, CA (US)

(*) Notice: Subject to any disclaimer, the term of this patent is extended or adjusted under 35 U.S.C. 154(b) by 372 days.

(21) Appl. No.: 15/052,612

(22) Filed: Feb. 24, 2016

(65) Prior Publication Data
US 2016/0281160 A1    Sep. 29, 2016

Related U.S. Application Data

(60) Provisional application No. 62/146,834, filed on Apr. 13, 2015, provisional application No. 62/119,996, filed on Feb. 24, 2015.

(51) Int. Cl.
*C12Q 1/6806*    (2018.01)
*C12Q 1/6869*    (2018.01)
*C12Q 1/6874*    (2018.01)

(52) U.S. Cl.
CPC ......... *C12Q 1/6874* (2013.01); *C12Q 1/6806* (2013.01); *C12Q 1/6869* (2013.01)

(58) Field of Classification Search
CPC ........ C12Q 2535/122; C12Q 2563/159; C12Q 2565/514; C12Q 1/6806; C12Q 1/6869; C12Q 1/6874
See application file for complete search history.

(56) References Cited

U.S. PATENT DOCUMENTS

| | | | |
|---|---|---|---|
| 2,797,149 A | 6/1957 | Skeggs | |
| 3,047,367 A | 7/1962 | Gerald | |
| 3,479,141 A | 11/1969 | Smythe et al. | |
| 4,124,638 A | 11/1978 | Hansen | |
| 4,253,846 A | 3/1981 | Smythe et al. | |
| 4,582,802 A | 4/1986 | Zimmerman et al. | |
| 5,137,829 A | 8/1992 | Nag et al. | |
| 5,149,625 A | 9/1992 | Church et al. | |

(Continued)

FOREIGN PATENT DOCUMENTS

| | | |
|---|---|---|
| CN | 103202812 A | 7/2013 |
| EP | 0249007 A2 | 12/1987 |

(Continued)

OTHER PUBLICATIONS

Jones, M.A. et al., Targeted polymerase chain reaction-based enrichment and next generation sequencing for diagnostic testing of congenital disorders of glycosylation, Gen. Med., vol. 13, pp. 921-932 (Year: 2011).*

(Continued)

*Primary Examiner* — Teresa E Strzelecka

(57) ABSTRACT

The present invention is directed to methods, compositions and systems for analyzing sequence information from targeted regions of a genome. Such targeted regions may include regions of the genome that are poorly characterized, highly polymorphic, or divergent from reference genome sequences.

26 Claims, 11 Drawing Sheets

(56) References Cited

U.S. PATENT DOCUMENTS

| | | |
|---|---|---|
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins |
| 5,708,153 A | 1/1998 | Dower et al. |
| 5,709,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,900,481 A | 5/1999 | Lough et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Thompson |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |

(56) References Cited

U.S. PATENT DOCUMENTS

| | | |
|---|---|---|
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Stone et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0051348 A1 | 12/2001 | Lee |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119536 A1 | 8/2002 | Stern |
| 2002/0119544 A1 | 8/2002 | Yan et al. |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0037397 A1 | 2/2005 | Mirkin et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0136417 A1 | 6/2005 | Cole et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0292583 A1 | 12/2006 | Schneider et al. |
| 2007/0003442 A1 | 1/2007 | Link et al. |
| 2007/0009954 A1 | 1/2007 | Wang et al. |
| 2007/0020617 A1 | 1/2007 | Trnovsky et al. |
| 2007/0020640 A1 | 1/2007 | McCloskey et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0141584 A1 | 6/2007 | Roberts et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |

(56) References Cited

U.S. PATENT DOCUMENTS

| | | |
|---|---|---|
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2008/0268507 A1 | 10/2008 | Xu et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston et al. |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston et al. |
| 2011/0092376 A1 | 4/2011 | Colston et al. |
| 2011/0092392 A1 | 4/2011 | Colston et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0289428 A1 | 11/2012 | Duffy et al. |
| 2012/0295819 A1* | 11/2012 | Leamon ............... C12Q 1/6806 506/26 |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0109596 A1 | 5/2013 | Peterson et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | DeSimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0274117 A1 | 10/2013 | Church et al. |
| 2013/0296173 A1 | 11/2013 | Callow et al. |
| 2013/0343317 A1 | 12/2013 | Etemad et al. |
| 2013/0344508 A1 | 12/2013 | Schwartz et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev |
| 2014/0120529 A1 | 5/2014 | Andersen et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206073 A1 | 7/2014 | Park et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |

(56) References Cited

U.S. PATENT DOCUMENTS

| | | |
|---|---|---|
| 2014/0357500 A1 | 12/2014 | Vigneault et al. |
| 2014/0357530 A1 | 12/2014 | Zhang et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0225786 A1 | 8/2015 | Litterst et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarssib et al. |
| 2016/0244809 A1 | 8/2016 | Belgrader et al. |
| 2016/0244811 A1 | 8/2016 | Edwards |
| 2016/0244825 A1 | 8/2016 | Vigneault et al. |
| 2016/0257984 A1 | 9/2016 | Hardenbol et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0087050 A1 | 3/2018 | Zheng et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0112253 A1 | 4/2018 | Hindson et al. |
| 2018/0179580 A1 | 6/2018 | Hindson et al. |
| 2018/0195112 A1 | 7/2018 | Lebofsky et al. |
| 2018/0216162 A1 | 8/2018 | Belhocine et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0274027 A1 | 9/2018 | Hindson et al. |
| 2018/0282803 A1 | 10/2018 | Belgrader et al. |
| 2018/0282804 A1 | 10/2018 | Hindson et al. |
| 2018/0335424 A1 | 11/2018 | Chen et al. |
| 2018/0376609 A1 | 12/2018 | Ju et al. |
| 2019/0071656 A1 | 3/2019 | Chang et al. |
| 2019/0153436 A1 | 5/2019 | Belhocine et al. |
| 2019/0153532 A1 | 5/2019 | Bharadwaj et al. |
| 2019/0177789 A1 | 6/2019 | Hindson et al. |
| 2019/0203262 A1 | 7/2019 | Hindson et al. |

FOREIGN PATENT DOCUMENTS

| | | |
|---|---|---|
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2752664 A1 | 7/2014 |
| EP | 2635679 B1 | 4/2017 |
| GB | 2097692 B | 5/1985 |
| GB | 2485850 A | 5/2012 |
| JP | 59-49832 A | 3/1984 |
| JP | S60227826 A | 11/1985 |
| JP | 2006-507921 A | 3/2006 |
| JP | 2006-289250 A | 10/2006 |
| JP | 2007015990 A | 1/2007 |
| JP | 2007-268350 A | 10/2007 |
| JP | 2009513948 A | 4/2009 |
| JP | 2009-208074 A | 9/2009 |
| JP | 2012131798 A | 7/2012 |
| WO | 1984002000 A1 | 5/1984 |
| WO | 1994018218 A1 | 8/1994 |
| WO | 1994019101 A1 | 9/1994 |
| WO | 1994023699 A1 | 10/1994 |
| WO | WO 1995030782 A1 | 11/1995 |
| WO | WO 1996029629 A2 | 9/1996 |
| WO | WO 1996041011 A2 | 12/1996 |
| WO | 1998002237 A1 | 1/1998 |
| WO | 1998052691 A1 | 11/1998 |
| WO | WO 1999009217 A1 | 2/1999 |
| WO | WO 1999052708 A1 | 10/1999 |
| WO | WO 2000008212 A1 | 2/2000 |
| WO | 2000023181 A1 | 4/2000 |
| WO | WO 2000026412 A1 | 5/2000 |
| WO | 2000043766 A1 | 7/2000 |
| WO | WO 2000070095 A2 | 11/2000 |
| WO | 2001002850 A1 | 1/2001 |
| WO | WO 2001014589 A2 | 3/2001 |
| WO | 2001090418 A1 | 11/2001 |
| WO | WO 2001089787 A2 | 11/2001 |
| WO | 2001027610 A3 | 3/2002 |
| WO | WO 2002031203 A2 | 4/2002 |
| WO | WO 2002086148 A1 | 10/2002 |
| WO | 2002018949 A3 | 1/2003 |

(56) References Cited

FOREIGN PATENT DOCUMENTS

| | | |
|---|---|---|
| WO | 2003062462 A2 | 7/2003 |
| WO | WO 2004002627 A2 | 1/2004 |
| WO | WO 2004010106 A2 | 1/2004 |
| WO | 2004061083 A2 | 7/2004 |
| WO | 2004065617 A2 | 8/2004 |
| WO | WO 2004069849 A2 | 8/2004 |
| WO | WO 2004091763 A2 | 10/2004 |
| WO | WO 2004102204 A1 | 11/2004 |
| WO | WO 2004103565 A2 | 12/2004 |
| WO | WO 2004105734 A1 | 12/2004 |
| WO | WO 2005002730 A1 | 1/2005 |
| WO | WO 2005021151 A1 | 3/2005 |
| WO | WO 2005023331 A2 | 3/2005 |
| WO | WO 2005040406 A1 | 5/2005 |
| WO | WO 2005049787 A2 | 6/2005 |
| WO | WO 2005082098 A2 | 9/2005 |
| WO | WO 2006030993 A1 | 3/2006 |
| WO | WO 2006078841 A1 | 7/2006 |
| WO | WO 2006096571 A2 | 9/2006 |
| WO | WO 2007001448 A2 | 1/2007 |
| WO | WO 2007002490 A2 | 1/2007 |
| WO | 2007012638 A1 | 2/2007 |
| WO | 2007018601 A1 | 2/2007 |
| WO | WO 2007024840 A2 | 3/2007 |
| WO | 2007084192 A2 | 7/2007 |
| WO | WO 2007081385 A2 | 7/2007 |
| WO | WO 2007081387 A1 | 7/2007 |
| WO | 2007093819 A2 | 8/2007 |
| WO | WO 2007089541 A2 | 8/2007 |
| WO | 2007111937 A1 | 10/2007 |
| WO | WO 2007114794 A1 | 10/2007 |
| WO | WO 2007121489 A2 | 10/2007 |
| WO | WO 2007133710 A2 | 11/2007 |
| WO | 2007147079 A2 | 12/2007 |
| WO | WO 2007138178 A2 | 12/2007 |
| WO | WO 2007139766 A2 | 12/2007 |
| WO | WO 2007140015 A2 | 12/2007 |
| WO | WO 2007149432 A2 | 12/2007 |
| WO | WO 2008021123 A1 | 2/2008 |
| WO | WO 2008091792 A2 | 7/2008 |
| WO | WO 2008102057 A1 | 8/2008 |
| WO | WO 2008109176 A2 | 9/2008 |
| WO | WO 2008121342 A2 | 10/2008 |
| WO | 2008061193 A3 | 11/2008 |
| WO | 2008135512 A2 | 11/2008 |
| WO | WO 2008134153 A1 | 11/2008 |
| WO | 2008150432 A1 | 12/2008 |
| WO | 2009015296 A1 | 1/2009 |
| WO | WO 2009005680 A1 | 1/2009 |
| WO | WO 2009011808 A1 | 1/2009 |
| WO | 2009048532 A2 | 4/2009 |
| WO | WO 2009061372 A1 | 5/2009 |
| WO | WO 2009085215 A1 | 7/2009 |
| WO | 2009147386 A1 | 12/2009 |
| WO | WO 2010004018 A2 | 1/2010 |
| WO | WO 2010033200 A2 | 3/2010 |
| WO | 2010048605 A1 | 4/2010 |
| WO | WO 2010104604 A1 | 9/2010 |
| WO | WO 2010115154 A1 | 10/2010 |
| WO | WO 2010148039 A2 | 12/2010 |
| WO | WO 2010151776 A2 | 12/2010 |
| WO | 2010117620 A3 | 2/2011 |
| WO | WO 2011028539 A1 | 3/2011 |
| WO | WO 2011047870 A1 | 4/2011 |
| WO | WO 2011056546 A1 | 5/2011 |
| WO | WO 2011066476 A1 | 6/2011 |
| WO | WO 2011074960 A1 | 6/2011 |
| WO | 2011140627 A1 | 11/2011 |
| WO | WO 2012012037 A1 | 1/2012 |
| WO | 2012047889 A2 | 4/2012 |
| WO | 2012048340 A2 | 4/2012 |
| WO | WO 2012048341 A1 | 4/2012 |
| WO | 2012061832 A1 | 5/2012 |
| WO | 2012112804 A1 | 8/2012 |
| WO | WO 2012106546 A2 | 8/2012 |
| WO | WO 2012112970 A2 | 8/2012 |
| WO | WO 2012083225 A2 | 9/2012 |
| WO | WO 2012136734 A1 | 10/2012 |
| WO | WO 2012142611 A2 | 10/2012 |
| WO | 2012148497 A2 | 11/2012 |
| WO | WO 2012149042 A2 | 11/2012 |
| WO | WO 2012166425 A2 | 12/2012 |
| WO | WO 2013019751 A1 | 2/2013 |
| WO | WO 2013036929 A1 | 3/2013 |
| WO | 2013055955 A1 | 4/2013 |
| WO | 2013096643 A1 | 6/2013 |
| WO | WO 2013122996 A1 | 8/2013 |
| WO | WO 2013123125 A1 | 8/2013 |
| WO | WO 2013126741 A1 | 8/2013 |
| WO | WO 2013134261 A1 | 9/2013 |
| WO | WO 2013150083 A1 | 10/2013 |
| WO | WO 2013/177220 A1 | 11/2013 |
| WO | 2013188872 A1 | 12/2013 |
| WO | WO 2014028537 A1 | 2/2014 |
| WO | 2014053854 A1 | 4/2014 |
| WO | 2014071361 A1 | 5/2014 |
| WO | WO 2014074611 A1 | 5/2014 |
| WO | WO 2014093676 A1 | 6/2014 |
| WO | 2014108810 A2 | 7/2014 |
| WO | 2014140309 A1 | 9/2014 |
| WO | 2014144495 A1 | 9/2014 |
| WO | 2014150931 A1 | 9/2014 |
| WO | 2014182835 A1 | 11/2014 |
| WO | 2014189957 A2 | 11/2014 |
| WO | WO 2014210353 A2 | 12/2014 |
| WO | 2015031691 A1 | 3/2015 |
| WO | WO 2015044428 A1 | 4/2015 |
| WO | 2014210353 A3 | 7/2015 |
| WO | WO 2015164212 A1 | 10/2015 |
| WO | 2016040476 A1 | 3/2016 |
| WO | 2016061517 A2 | 4/2016 |
| WO | 2016126871 A2 | 8/2016 |
| WO | 2016126871 A3 | 10/2016 |
| WO | 2016187717 A1 | 12/2016 |
| WO | 2016191618 A1 | 12/2016 |
| WO | 2016207647 A1 | 12/2016 |
| WO | 2016207653 A1 | 12/2016 |
| WO | 2016207661 A1 | 12/2016 |
| WO | 2017015075 A1 | 1/2017 |
| WO | 2017025594 A1 | 2/2017 |
| WO | 2017053905 A1 | 3/2017 |
| WO | 2017075265 A1 | 5/2017 |
| WO | 2017151828 A1 | 9/2017 |
| WO | 2017156336 A1 | 9/2017 |
| WO | 2017180420 A1 | 10/2017 |
| WO | 2018045186 A1 | 3/2018 |
| WO | 2019084328 A1 | 5/2019 |
| WO | 2019099751 A1 | 5/2019 |

OTHER PUBLICATIONS

Hu< H et al., Mutation screening in 86 known X-linked mental retardation genes by droplet-based multiplex PCR and massive parallel sequencing, Hugo J., vol. 3, pp. 41-49 (Year: 2009).*
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth2688. Epub Oct. 5, 2013.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatoryvariation. Nature. Jul. 3, 2015;523(7561):486-90. doi: 10.1038/nature14590. Epub Jun. 17, 2015.
Burns, Jr. et al. "The intensification of rapid reactions in multiphase systems using slug flow in capillaries" Lab Chip. (Sep. 2001) 1(1):10-15.
Burns, M.A. et al. "An Integrated Nanoliter DNA Analysis Device" Science (1998) 282:484-487.
Burns, M.A. et al. "Microfabricated structures for integrated DNA analysis" PNAS (1996) 93(11):5556-5561.

(56) References Cited

OTHER PUBLICATIONS

Caruccio, N., "Preparation of Next-Generation Sequencing Libraries Using Nextera Technology: Simultaneous DNA Fragmentation and Adaptor Tagging by In Vitro Transposition." Ch. 17 Methods in Microbiology 733:241 (2011).
Casbon, et al, "Reflex: intramolecular barcoding of long-range PCR products for sequencing multiple pooled DNAs", Nucleic Acids Res, pp. 1-6, 2013.
Clark, et al. Single-cell epigenomias: powerful new methods for understanding gene regulation and cell identity. Genome Biol. Apr. 18, 2016;17:72. doi: 10.1186/s13059-016-0944-x.
Co-pending U.S. Appl. No. 15/596,754, filed May 16, 2017.
Co-pending U.S. Appl. No. 15/687,357, filed Aug. 25, 2017.
"Portable Water Filters" (http://www.portablewaterfilters.org/water-filter-guide/particle-contaminant-size-chart-microns/) 2015, accessed Oct. 19, 2017. (Year: 2015).
Adey, et al. Rapid, low-input, low-bias construction of shotgun fragment libraries by high-density in vitro transposition. Genome Biology 11 :R119 (2010).
Ahern, "Biochemical, Reagents Kits Offer Scientists Good Return on Investment" The Scientist (1995) 9(15):1-7.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi:10.1038/nbt.3662. Epub Aug. 29, 2016.
Boulanger, et al., "Massively parallel haplotyping on microscopic beads for the high-throughput phase analysis of single molecules", PLoS One, vol. 7:1-10, 2012.
Brown, K., Targeted Sequencing Using Droplet-Based Microfluidics, RainDance Technologies, 2009, 1-18.
Buchman, GW et al. "Selective RNA amplification: a novel method using dUMP-containing primers and uracil DNA glycosylase" PCR Methods Appl. Aug. 1993; 3(1):28-31.
Co-Pending U.S. Appl. No. 15/831,847, filed Dec. 5, 2017.
Co-Pending U.S. Appl. No. 15/832,183, filed Dec. 5, 2017.
Co-Pending U.S. Appl. No. 15/832,547, filed Dec. 5, 2017.
Co-Pending U.S. Appl. No. 15/842,550, filed Dec. 14, 2017.
Co-Pending U.S. Appl. No. 15/842,687, filed Dec. 14, 2017.
Co-Pending U.S. Appl. No. 15/842,713, filed Dec. 14, 2017.
Co-Pending U.S. Appl. No. 15/847,659, filed Dec. 19, 2017.
Co-Pending U.S. Appl. No. 15/847,752, filed Dec. 19, 2017.
Co-Pending U.S. Appl. No. 15/848,714, filed Dec. 20, 2017.
Co-Pending U.S. Appl. No. 15/850,241, filed Dec. 21, 2017.
Co-Pending U.S. Appl. No. 15/872,499, filed Jan. 16, 2018.
Co-Pending U.S. Appl. No. 15/687,856, filed Aug. 28, 2017.
Co-Pending U.S. Appl. No. 15/693,374, filed Aug. 31, 2017.
Co-Pending U.S. Appl. No. 15/717,840, filed Sep. 27, 2017.
Co-Pending U.S. Appl. No. 15/717,847, filed Sep. 27, 2017.
Co-Pending U.S. Appl. No. 15/717,871, filed Sep. 27, 2017.
Co-Pending U.S. Appl. No. 15/718,764, filed Sep. 28, 2017.
Co-Pending U.S. Appl. No. 15/718,893, filed Sep. 28, 2017.
Co-Pending U.S. Appl. No. 15/719,459, filed Sep. 28, 2017.
Co-Pending U.S. Appl. No. 15/720,085, filed Sep. 29, 2017.
Co-Pending U.S. Appl. No. 15/825,740, filed Nov. 29, 2017.
Co-Pending U.S. Appl. No. 15/831,726, filed Dec. 5, 2017.
Curcio, M. "Improved Techniques for High-Throughput Molecular Diagnostics" Royal Institute of Technology (2002) Ph.D. Thesis.
Cusanovich, et al. Supplementary materials for Multiplex single-cell profiling of chromatin accessibility by combinatorial cellular indexing. Science. May 22, 2015;348(6237):910-4. doi:10.1126/science.aab1601. Epub May 7, 2015.
Cusanovich; et al., "Multiplex single-cell profiling of chromatin accessibility by combinatorial cellular indexing." Sciencexpress, May 7, 2014, p. 1-9.
Damean, N. et al. "Simultaneous measurement of reactions in microdroplets filled by concentration gradients" Lab Chip (Jun. 21, 2009) 9(12):1707-1713.
Dey, et al. "Integrated Genome and Transcriptome Sequencing from the Same Cell." Nature biotechnology 33.3 (2015): 285-289. PMC Web. Dec. 18, 2017.
Dressman et al. Supplementary Information pp. 1-2 of article published 2003, PNAS 100(15:8817-22).
Hamilton, A.J. "microRNA in erythrocytes" Biochem. Soc. Trans. (2010) 38, 229-231.
Han, X. et al. "CRISPR-Cas9 delivery to hard-to-transfect cells via membrane deformation" Science Advances (2015) 1(7): E1500454 (8 pages).
Hiatt, et al., "Parallel, tag-directed assembly of locally derived short sequence reads", Nat Methods., 7:119-122, 2010.
Anna et al., "Formation of dispersions using 'flow focusing' in microchannels", Appln. Phys. Letts. 82:3 364 (2003).
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Attia, U.M et al., "Micro-injection moulding of polymer microfluidic devices" Microfluidics and nanofluidics (2009) 7(1):1-28.
Baret et al. "Fluorescence-activated droplet sorting (FADS): efficient microfluidic cell sorting based on enzymatic activity" Lab on a Chip (2009) 9(13):1850-1858.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Brouzes, E et al., "Droplet microfluidic technology for single-cell high-throughput screening" PNAS (2009) 106(34):14195-14200.
Abate et al., Valve-based flow focusing for drop formation. Appl Phys Lett. 2009;94. 3 pages.
Abate, A.R. et al. "Beating Poisson encapsulation statistics using close-packed ordering" Lab on a Chip (Sep. 21, 2009) 9(18):2628-2631.
Abate, et al. High-throughput injection with microfluidics using picoinjectors. Proc Natl Acad Sci U S A. Nov. 9, 2010; 107(45):19163-6. doi: 10.1073/pNas.1006888107. Epub Oct. 20, 2010.
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Akselband, "Enrichment of slow-growing marine microorganisms from mixed cultures using gel microdrop (GMD) growth assay and fluorescence-activated cell sorting", J. Exp. Marine Biol., 329:196-205 (2006).
Akselband, "Rapid mycobacteria drug susceptibility testing using gel microdrop (GMD) growth assay and flow cytometry", J. Microbiol. Methods, 62:181-197 (2005).
Demirci, et al. "Single cell epitaxy by acoustic picolitre droplets" Lab Chip. Sep. 2007;7(9):1139-45. Epub Jul. 10, 2007.
Doerr, "The smallest bioreactor", Nature Methods, 2:5 326 (2005).
Doshi, N. et al. "Red blood cell-mimicking synthetic biomaterial particles" PNAS (2009) 106(51):21495-21499.

(56) References Cited

OTHER PUBLICATIONS

Dowding, et al. "Oil core/polymer shell microcapsules by interNal phase separation from emulsion droplets. II: controlling the release profile of active molecules" Langmuir. Jun. 7, 2005;21(12):5278-84.
Draper, M.C. et al., "Compartmentalization of electrophoretically separated analytes in a multiphase microfluidic platform" Anal. Chem. (2012) 84:5801-5808.
Dressler, O.J. et al., "Droplet-based microfluidics enabling impact on drug discovery" J. Biomol. Screen (2014) 19(4):483-496.
Drmanac et al., Sequencing by hybridization (SBH): advantages, achievements, and opportunities. Adv Biochem Eng Biotechnol. 2002;77:75-101.
Droplet Based Sequencing (slides) dated (Mar. 12, 2008).
Eastburn, D.J. et al., "Ultrahigh-throughput mammalian single-cell reverse-transcriptase polymerase chain reaction in microfluidic droplets" Anal. Chem. (2013) 85:8016-8021.
Esser-Kahn, et al. Triggered release from polymer capsules. Macromolecules. 2011; 44:5539-5553.
Fan, et al. Noninvasive diagnosis of fetal aneuploidy by shotgun sequencing DNA from maternal blood. Proc Natl Acad Sci U S A. Oct. 21, 2008;105(42):16266-71. doi: 10.1073/pnas.0808319105. Epub Oct. 6, 2008.
Carroll, "The selection of high-producing cell lines using flow cytometry and cell sorting", Exp. Op. Bioi. Therp., 4:11 1821-1829 (2004).
Chaudhary "A rapid method of cloning functional variable-region antibody genes in *Escherichia coli* as single-chain immunotoxins" Proc. Nat!. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;l8(1):83-101.
Chen, F et al., "Chemical transfection of cells in picoliter aqueous droplets in fluorocarbon oil" Anal. Chem. (2011) 83:8816-8820.
Chokkalingam, V et al., "Probing cellular heterogeneity in cytokine-secreting immune cells using droplet-based microfluidics" Lab Chip (2013) 13:4740-4744.
Chou, H-P. et al. "Disposable Microdevices for DNA Analysis and Cell Sorting" Proc. Solid-State Sensor and ActuatorWorkshop Hilton Head, SC Jun. 8-11, 1998, pp. 11-14.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, L-Y. et al., "Controllable monodisperse multiple emulsions" Angew. Chem. Int. Ed. (2007) 46:8970-8974.
Clausell-Tormos et al., "Droplet-based microfluidic platforms for the encapsulation and screening of mammalian cells and multicellular organisms", Chem. Biol. 15:427-437 (2008).
Coufal, et al. L1 retrotransposition in human neural progenitor cells. Nature. Aug. 27, 2009;460(7259): 1127-31. doi: 10.1038/nature08248. Epub Aug. 5, 2009.
De Bruin et al., UBS Investment Research. Q-Seriesï¿½: DNa Sequencing. UBS Securities LLC. Jul. 12, 2007. 15 pages.
Granieri, Lucia "Droplet-based microfluidics and engineering of tissue plasminogen activator for biomedical applications" Ph.D. Thesis, Nov. 13, 2009 (131 pages).
Grasland-Mongrain, E. et al. "Droplet coalescence in microlfuidic devices" Internet Citation, 2003, XP002436104, Retrieved from the Internet: URL:http://www.eleves.ens.fr./home/grasland/rapports/stage4.pdf [retrieved on Jun. 4, 2007].
Guo, M.T. et al., "Droplet microfluidics for high-throughput biological assays" Lab Chip (2012) 12:2146-2155.
Gyarmati et al., "Reversible Disulphide Formation in Polymer Networks: A Versitile Functional Group from Synthesis to Application," European Polymer Journal, 2013, 49, 1268-1286.
Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.

He "Selective Encapsulation of Single Cells and Subcellular Organelles into Picoliter- and Femtoliter-Volume Droplets" Anal. Chern 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hjerten, S. et al. "General methods to render mcaroporous stationary phases nonporous and deformable, exemplified with agarose and silica beads and their use in high-performance ion-exchange and hydrophobic-interaction chromatography of proteins" Chromatographia (Jan. 1991) 31(1-2):85-94.
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Huebner, "Quantitative detection of protein expression in single cells using droplet microfluidics", Chern. Commun. 1218-1220 (2007).
Hug, H. et al. "Measurement of the No. of molecules of a single mRNA species in a complex mRNA preparation" J Theor Biol. Apr. 21, 2003;221(4):615-24.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, S. et al. "A Scalable, fully automated process for construction of sequence-ready human exome targeted capture libraries" Genome Biology (2011) 2:R1-R15. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, C.K. et al., "Macro-to-micro interfaces for microfluidic devices" Lab Chip (2004) 4:526-533.
Freiberg, et al. "Polymer microspheres for controlled drug release" Int J Pharm. Sep. 10, 2004;282(1-2):1-18.
Fu. A.Y. et al. "A microfabricated fluorescence-activated cell sorter" Nature Biotech (Nov. 1999) 17:1109-1111.
Fulton et al., "Advanced multiplexed analysis with the FlowMetrix system" Clin Chern. Sep. 1997;43(9): 1749-56.
Garstecki, P. et al. "Formation of monodisperse bubbles in a microfluidic flow-focusing device" Appl. Phys. Lett (2004) 85(13):2659-2651. DOI: 10.1063/1.1796526.
Gartner, et al. The Microfluidic Toolbox ï¿½ examples for fluidic interfaces and standardization concepts. Proc. SPIE 4982, Microfluidics, BioMEMS, and Medical Microsystems, (Jan. 17, 2003); doi: 10.1117/12.479566.
Gericke, M. et al. "Functional Cellulose Beads: Preparation, Characterization, and Applications" Chem Rev (2013) 113(7):4812-4836.
Ghadessy, et al. Directed evolution of polymerase function by compartmentalized self-replication. Proc Natl Acad Sci U S A. Apr. 10, 2001;98(8):4552-7. Epub Mar. 27, 2001.
Li, Y., et al., "PEGylated PLGA Nanoparticles as protein carriers: synthesis, preparation and biodistribution in rats," Journal of Controlled Release, vol. 71, pp. 203-211 (2001).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24(6)703-707 (Jun. 2006).
Lowe, Adam J."Norbornenes and [n]polynorbornanes as molecular scaffolds for anion recognition" Ph.D. Thesis (May 2010). (361 pages).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.

(56) References Cited

OTHER PUBLICATIONS

Mair, D.A. et al., "Injection molded microfluidic chips featuring integrated interconnects" Lab Chip (2006) 6:1346-1354.
Makino, K. et al. "Preparation of hydrogel microcapsules Effects of preparation conditions upon membrane properties" Colloids and Surfaces: B Biointerfaces (1998) 12:97-104.
Marcus. Gene method offers diagnostic hope. The Wall Street Journal. Jul. 11, 2012.
Matochko, W.L. et al., "Uniform amplification of phage display libraries in monodisperse emulsions," Methods (2012) 58:18-27.
Ioannidis, N "Manufacturing of agarose-based chromatographic media with controlled pore and particle size" (2009) XP055289233, Retrieved from the Internet: URL: http://etheses.bham.ac.Uk/368/3/Ioannidis09PhD.pdf.
Jena et al., "Cyclic olefin copolymer based microfluidic devices for biochip applications: Ultraviolet surface grafting using 2-methacryloyloxyethyl phosphorylchloline" Biomicrofluidics (Mar. 15, 2012) 6:012822 (12 pages).
Jung, W-C et al., "Micromachining of injection mold inserts for fluidic channel of polymeric biochips" Sensors (2007) 7:1643-1654.
Khomiakov A et al., "Analysis of perfect and mismatched DNA duplexes by a generic hexanucleotide microchip". Mol Bioi (Mosk). Jul.-Aug. 2003;37(4):726-41. Russian. Abstract only.
Kim, et al. Albumin loaded microsphere of amphiphilic poly(ethylene glycol)/ poly(alpha-ester) multiblock copolymer. Eur J Pharm Sci. Nov. 2004;23(3):245-51.
Kim, et al. Fabrication of monodisperse gel shells and functioNal microgels in microfluidic devices. Angew Chem Int Ed Engl. 2007;46(11):1819-22.
Kim, J et al., "Rapid prototyping of microfluidic systems using a PDMS/polymertape composite" Lab Chip (2009) 9:1290-1293.
Klein, et al. Droplet barcoding for single-cell transcriptomics applied to embryonic stem cells. Cell. May 21, 2015; 161:1187-1201.
Koster et al., "Drop-based microfluidic devices for encapsulation of single cells", Lab on a Chip The Royal Soc. of Chern. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagus, T.P. et al., "A review of the theory, methods and recent applications of high-throughput single-cell droplet microfluidics" J. Phys. D: Appl. Phys. (2013) 46:114005 (21 pages).
Navin, N.E. "The first five years of single-cell cancer genomics and beyond" Genome Res. (2015) 25:1499-1507.
Nguyen, et al. In situ hybridization to chromosomes stabilized in gel microdrops. Cytometry. 1995; 21:111-119.
Novak, R. et al., "Single cell multiplex gene detection and sequencing using microfluidicallygenerated agarose emulsions" Angew. Chem. Int. Ed. Engl. (2011) 50(2):390-395.
Oberholzer, et al. Polymerase chain reaction in liposomes. Chern Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, "Controlled production of monodisperse double emulsions by two-step droplet breakup in microfluidic devices", Langmuir, 20:9905-9908 (2004).
Pantel, et al. Detection methods of circulating tumor cells. J Thorac Dis. Oct. 2012;4(5):446-7. doi: 10.3978/j.issn.2072-1439.2012.08.15.
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery ofplasmid DNa," Journal of Controlled Release, vol. 75, pp. 211-224 (2001).
Peters et al., "Accurate whole-genome sequencing and haplotyping from 10 to 20 human cells," Nature, Jul. 12, 2012, vol. 487, pp. 190-195.

Picot, J. et al. "A biomimetic microfluidic chip to study the circulation and mechanical retention of red blood cells in the spleen" Am J Hematology (Jan. 12, 2015) 90(4):339-345.
Mazutis, et al. Selective droplet coalescence using microfluidic systems. Lab Chip. Apr. 24, 2012;12(10):1800-6. doi: 10.1039/c2lc40121e. Epub Mar. 27, 2012.
Merriman, et al. Progress in ion torrent semiconductor chip based sequencing. Electrophoresis. Dec. 2012;33(23):3397-3417. doi: 10.1002/elps.201200424.
Microfluidic ChipShop. Microfluidic product catalogue. Mar. 2005.
Microfluidic ChipShop. Microfluidic product catalogue. Oct. 2009.
Mirzabekov, "DNA Sequencing by Hybridization—a Megasequencing Method and A Diagnostic Tool?" Trends in Biotechnology 12(1): 27-32 (1994).
Moore, J.L. et al., "Behavior of capillary valves in centrifugal microfluidic devices prepared by three-dimensional printing" Microfluid Nanofluid (2011) 10:877-888.
Morgan, et al. Chapter 12: Human microbiome analysis. PLoS Comput Biol. 2012;8(12):e1002808. doi: 10.1371/journal.pcbi. 1002808. Epub Dec. 27, 2012.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Nagashima, S. et al. "Preparation of monodisperse poly(acrylamide-co-acrylic acid) hydrogel microspheres by a membrane emulsification technique and their size dependent surface properties" Colloids and Surfaces: B Biointerfaces (1998) 11:47-56.
Shah, "Fabrication of mono disperse thermosensitive microgels and gel capsules in micro fluidic devices", Soft Matter, 4:2303-2309 (2008).
Shimkus et al. "A chemically cleavable biotinylated nucleotide: Usefulness in the recovery of protein-DNA complexes from avidin affinity columns" PNAS (1985) 82:2593-2597.
Shuttleworth, et al. "Recognition of the pro-mutagenic base uracil by family B DNA polymerases from archaea" J Mol Biol (Mar. 26, 2004) 337(3):621-634.
Simeonov et al., Single nucleotide polymorphism genotyping using short, fluorescently labeled locked nucleic acid (LNa) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodyNamic and kinetic effects during hybridization. J Biomol Struct Dyn. Jun. 2005;22(6):725-34.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S. et al. "Man-made cell-like compartments for molecular evolution" Nature Biotech (Jul. 1998) 16:652-656.
Tayyab, S. et al. "Size exclusion chromatography and size exclusion HPLC of proteins" Biochem Ed, Pergamon, (1991) 19(3):149-152.
Tewhey, R. et al., "Microdroplet-based PCR enrichment for large-scale targeted sequencing" Nature Biotech. (2009) 27(11):1025-1031 and Online Methods (11 pages).
Theberge, A.B, et al. Microdropelts in microfluidics: an evolving platform for discoveries in chemsitry and biology. Angew Chem Int Ed Engl. Aug. 9, 2010;49(34):5846-68. doi: 10.1002/anie.200906653.
Plunkett, et al. Chymotrypsin responsive hydrogel: application of a disulfide exchange protocol for the preparation of methacrylamide containing peptides. Biomacromolecules. Mar.-Apr. 2005;6(2):632-7.

(56) References Cited

OTHER PUBLICATIONS

Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011. 555598. Epub Mar. 1, 2011.
Richardson, T.T. et al. "Novel inhibition of archaeal family-D DNA polymerase by uracil" Nucl Acids Res (2013) 41(7):4207-4218.
Rogozin, I.B. et al. "A highly conserved family of inactivated archaeal B family DNA polymerases" Biology Direct (2008) 3:32-36.
Rotem, A. et al. "Single Cell Chip-Seq Using Drop-Based Microfluidics" Abstract #50. Frontiers of Single Cell Analysis, Stanford University Sep. 5-7, 2013.
Rotem, A. et al., "High-throughput single-cell labeling (Hi-SCL) for RNA-Seq using drop-based microfluidics" PLOS One (May 22, 2015) 0116328 (14 pages).
Ryan, et al. Rapid assay for mycobacterial growth and antibiotic susceptibility using gel microdrop encapsulation. J Clin Microbiol. Jul. 1995;33(7):1720-6.
Schirinzi et al., Combinatorial sequencing-by-hybridization: analysis of the NF1 gene. Genet Test. 2006 Spring;10(1):8-17.
Schmieder, R. et al. "Fast Identification and Removal of Sequence Contamination from Genomic and Metagenomic Datasets" PLoS ONE, (Mar. 9, 2011) 6(3):1-11.
Schmitt, "Bead-based multiplex genotyping of human papillomaviruses", J. Clinical Microbiol., 44:2 504-512 (2006).
Seiffert, S. et al., "Smart microgel capsules from macromolecular precursors" J. Am. Chem. Soc. (2010) 132:6606-6609.
Yamamoto, et al. Chemical modification of Ce(IV)/EDTA-base artificial restriction DNa cutter for versatile manipulation ofdoulbe-stranded DNa. Nucleic Acids Research. 2007; 35(7):e53.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functioNalized nucleosides via the RAFT process. Biomacromolecules. Nov. 2008;9(11):3321-31. doi: 10.1021/bm800867n. Epub Oct. 9, 2008.
Zhao, J., et al., "Preparation of hemoglobin-loaded Nano-sized particles with porous structure as oxygen carriers," Biomaterials, vol. 28, pp. 1414-1422 (2007).
Zhu, S. et al., "Synthesis and self-assembly of highly incompatible polybutadienepoly(hexafluoropropoylene oxide) diblock copolymers" J. Polym. Sci. (2005) 43:3685-3694.
Zimmermann et at., Microscale production of hybridomas by hypoosmolar electrofusion. Human Antibodies Hybridomas. Jan. 1992; 3(1 ): 14-8.
Zong, C. et al. "Genome-wide detection of single-nucleotide and copy-number variations of a single human cell" Science. Dec. 21, 2012;338(6114):1622-6. doi: 10.1126/science.1229164.
Tonelli, C. et al., "Perfluoropolyether functional oligomers: unusual reactivity in organic chemistry" J. Fluorine Chem. (2002) 118:107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. "Methods for genomic partitioning" Annu Rev Genomics Human Genet. (2009) 10:263-284. doi: 10.1146/annurev-genom-082908-150112. Review.
Wagner, O et al., "Biocompatible fluorinated polyglycerols for droplet microfluidics as an alternative to PEG-based copolymer surfactants" Lab Chip DOI:10.1039/C5LC00823A. (2015).
Wang et al., Single nucleotide polymorphism discrimination assisted by improved base stacking hybridization using oligonucleotide microarrays. Biotechniques. 2003;35:300-08.
Wang, et al. A novel thermo-induced self-bursting microcapsule with magnetic-targeting property. Chemphyschem. Oct. 5, 2009;10(14):2405-9.
Weaver, J.C. et al. "Rapid clonal growth measurements at the single-cell level: gel microdroplets and flow cytometry", Biotechnology, 9:873-877 (1991).
Whitesides, "Soft lithography in biology and biochemistry", Annual Review of Biomedical Engineering, 3:335-373 (2001).
Williams, R. et al. "Amplification of complex gene libraries by emulsion PCR" Nature Methods (Jul. 2006) 3(7):545-550.
Woo, et al. G/C-modified oligodeoxynucleotides with selective complementarity: synthesis and hybridization properties. Nucleic Acids Res. Jul. 1, 1996;24(13):2470-5.
Xia, "Soft lithography", Annual Review of Material Science, 28: 153-184 (1998).
Thorsen, T. et al. "Dynamic Pattern Formation in a Vesicle-Generating Microfluidic Device" Phys Rev Letts (Apr. 30, 2001) 86(18):4163-4166.
Turner, et al, "Assaying chromosomal inversions by single molecule haplotyping", Nat Methods., 3:439-445, 2006.
Turner, et al, "High-throughput haplotype determination over long distances by haplotype fusion PCR and ligation haplotyping", Nat Protoc., 4:1771-83, 2009.
Ushijima et al., Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wang; et al., "Self-Formed Adaptor PCR: a Simple and Efficient Method for Chromosome Walking", Applied and Environmental Microbiology (Aug. 2007), 73(15):5048-5051.
Ward, T. et al. "Microfluidic flow focusing: drop size and scaling in pressure versus flow-rate-driven pumping" Electrophoresis (2005) 26(19):3716-3724.
Weigl, B.H. et al. "Microfluidic Diffusion-Based Separation and Detection" Science (Jan. 15, 1999) 283 (5400):346-347.
Wiseman, R.W. et al. "Major histocompatibility complex genotyping with massively parallel pyrosequencing" Nature Medicine (Oct. 11, 2009) 15(11):1322-1326.
Xi, L. et al. "New library construction methods for single-cell genomes" PLOS (2017) 12(7):e0181163.
Xiao, et al., "Determination of haplotypes from single DNA molecules: a method for single-molecule barcoding", Hum Mutat., 28:913-21, 2007.
Yan, Pu et al. "Rapid on-step construction of hairpin RNA" Biochem and Biophys Res Comm (Jun. 12, 2009) 383(4):464-468.
Zeng, Y. et al. "High-Performance Single Cell Genetic Analysis Using Microfluidic Emulsion Generator Arrays" Analytical Chemistry (Apr. 15, 2010) 82(8):3183-3190.
Zerbino, Daniel, "Velvet Manual—version 1.1," Aug. 15, 2008, pp. 1-22.
Zhang. Genomics of inherited bone marrow failure and myelodysplasia. Dissertation [online]. University of Washington. 2015 [Retrieved on May 3, 2017].
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilizedperturb-seq-approach/.
Adamson et al., "Production of arrays of chemically distinct nanolitre plugs via repeated splitting in microfluidic devices", Lab Chip 6(9): 1178-1186 (Sep. 2006).
Adamson, et al. A Multiplexed Single-Cell CRISPR Screening Platform Enables Systematic Dissection of the Unfolded Protein Response. Cell. Dec. 15, 2016; 167(7): 1867-1882.e21. doi: 10.1016/j.cell.2016.11.048.
Brenner, et al. "In vitro cloning of complex mixtures of DNA on microbeads: physical separation of differentially expressed cDNAs." Proc Natl Acad Sci USA. Feb. 15, 2000;97(4):1665-70.
Chang et al. "Droplet-based microfluidic platform for heterogeneous enzymatic assays" LabChip (2013) 13:1817-1822.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.

(56) References Cited

OTHER PUBLICATIONS

Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Han, S-E et al. "Targeted Sequencing of Cancer-Related Genes in Colorectal Cancer Using Next-Generation Sequencing" PLOS One (2013) 8(5):e64271.

Ilumina, Inc. An Introduction to Next-Generation Sequencing Technology. Feb. 28, 2012.

JPK "Determining the elastic modulus of biological samples using atomic force microscopy" (https://www.jpk.com/app-technotes-img/AFM/pdf/jpk-app-elastic-modulus. 14-1.pdf) 2009, pp. 1-9 (Year: 2009).

Kolodeziejczyk et al., "The technology and biology of single-cell RNA sequencing", Molecular Cell, vol. 58 (May 21, 2015).

Lasken et al. "Archaebacterial DNA Polymerases Tightly Bind Uracil-containing DNA" The Journal of Biological Chemistry (1996) 271 (30):17692-17696.

Lee, K. Y. et al. "Alginate: properties and biomedical applications" Prog Polym Sci. Jan. 2012; 37(1): 106-126.

Miller-Stephenson Chemicals 157 FS Series catalog, www.miller-stephenon.com.

Morimoto, Y. et al. "Monodisperse semi-permeable microcapsules for continuous observation of cells" LabChip (2009) 9(15):2217-2223.

Narayanan, J. et al. "Determination of agarose gel pore size: Absorbance measurements vis a vis other techniques" Journal of Physics: Conference Series 28 (2006) 83-86.

Sakaguchi et al. "Cautionary Note on the Use of dUMP-Containing PGR Primers with Pfu and VentR". BioTechniques (1996) 21(3):369-370.

Spormann Laboratory, Polymerase Chain Reaction (PCR), Alfred Spormann Laboratory, 2009, 1-3.

Thermofisher, Protocols, M-270 Streptavidin, ThermoFisherScientific, 2007, 1-5. (Year: 2007).

Xia and Whitesides, Soft Lithography, Angew. Chem. Int. Ed. 37:550-575 (1998).

Zhou, Y. et al. "Development of an enzyme activity screening system for (3-glucosidase-displaying yeasts using calcium alginatemicrobeads and flow sorting" Appl Microbiol Biotechnol (2009) 84:375-382.

Zhu, YY et al. "Reverse transcriptase template switching: a SMART approach for full-length cDNA library construction" Biotechniques (2001) 30(4):892-897.

International Search Report for International Patent Application No. PCT/US2016/019382, dated Jun. 3, 2016, 12 pages.

Altemose et al., "Genomic Characterization of Large Heterochromatic Gaps in the Human Genome Assembly," PLOS Computational Biology, May 15, 2014, col. 10, Issue 5, 14 pages.

Amini et al., "Haplotype-resolved whole genome sequencing by contiguity preserving transposition and combinatorial indexing," Nature Genetics, 2014, vol. 46, pp. 1343-1349.

Lee et al., "Fluorescent in situ sequencing (FISSEQ) of RNA for gene expression profiling in intact cells and tissues," Nature Protocols, vol. 10, No. 3, Feb. 12, 2015, pp. 442-458.

Zheng et al., "Halotyping germline and cancer genomes with high-throughput linked-read sequencing," Nature Biology, vol. 34, No. 3, Feb. 1, 2016, pp. 303-311.

Aitman, et al. Copy number polymorphism in Fcgr3 predisposes to glomerulonephritis in rats and humans. Nature. Feb. 16, 2006;439(7078):851-5.

Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.

Berkum et al., "Hi-C: A Method to Study the Three-dimensional Architecture of Genomes," J Vis Exp (39), e1896, doi:10.3791/1869 (2010).

Biles et al., Nucl. Acids Res. 32(22):e176 2004.

Briggs, et al. "Tumor-infiltrating immune repertoires captures by single-cell barcoding in emulsion" with Supplementary material. bioRxiv 134841; doi: https://doi.org/10.1101/134841. Posted May 5, 2017.

Browning, S.R. et al. "Haplotype Phasing: Existing Methods and New Developments" NaRevGenet (Sep. 16, 2011) 12(10):703-714.

Cappuzzo, et al. Increased HER2 gene copy No. is associated with response to gefitinib therapy in epidermal growth factor receptor-positive non-small-cell lung cancer patients. J Clin Oncol. Aug. 1, 2005 ;23(22):5007-18.

Choi et al. "Identification of novel isoforms of the EML4-ALK transforming gene in non-small cell lung cancer," Cancer Res (2008) 68:4971-4976.

Christian M, et al. Targeting DNA double-strand breaks with TAL effector nucleases Genetics. (2010) 186:757-761.

Chung et al., "Structural and molecular interrogation of intact biological systems," Nature, May 16, 2013, 23 page.

Cong et al., "Multiplex Genome Engineering Using CRISPR/Cas Systems," Science, Feb. 15, 2013, vol. 339, No. 6121, pp. 819-823.

Cook, et al. Copy-number variations associated with neuropsychiatric conditions. Nature. Oct. 16, 2008;455(7215):919-23. doi: 10.1038/nature07458.

Co-pending U.S. Appl. No. 15/392,557, filed Dec. 28, 2016.
Co-pending U.S. Appl. No. 15/430,298, filed Feb. 10, 2017.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/470,814, filed Mar. 27, 2017.
Co-pending U.S. Appl. No. 15/588,519, filed May 5, 2017.
Co-pending U.S. Appl. No. 15/598,898, filed May 18, 2017.

Dekker et al., "Capturing chromosome conformation," Science 295:1306-1311 (2002).

Dressman et al. "Transforming single DNA molecules into fluorescent magnetic particles for detection and enumeration of genetic variations" PNAS (2003) 100(15):8817-8822.

Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.

Fan, et al. "Whole-genomre molecular haplotyping of single cells," Nature Biotechnology, vol. 29 No. 1, Jan. 2011.

Gonzalez, et al. The influence of CCL3L1 gene-containing segmental duplications on HIV-1/AIDS susceptibility. Science. Mar. 4, 2005;307(5714):1434-40. Epub Jan. 6, 2005.

Hirsch et al. "Easily reversible desthiobiotin binding to streptavidin, avidin, and other biotin-binding proteins: uses for protein labeling, detection, and isolation" Analytical Biochem (2002) 308(2) :343-357.

Illumina TrueSeq Custom Enrichment Kit, pp. 1-4 (2011-2012).

Kaper et al., PNAS, vol. 110, pp. 5552-5557 (Apr. 2013).

Kaper et al., PNAS, vol. 110, (Apr. 2013) Supplemental date pp. 1-7.

Karmakar et al., "Organocatalytic removal of formaldehyde adducts from RNA and DNA bases," Nature Chemistry, 2015, doi:10.1038/nchm.2307.

Kebschull et al., "High-Throughput Mapping of Single-Neuron Projections by Sequencing of Barcoded RNA," Neuron, vol. 91, Issue 5, Sep. 7, 2016, p. 975-987.

Kitzman, et al. Noninvasive whole-genome sequencing of a human fetus. Sci Transl Med. Jun. 6, 2012;4(137):137ra76.doi: 10.1126/scitranslmed.3004323.

Kivioj, A. et al., "Counting Absolute Nos. of Molecules Using Unique Molecular Identifiers", Nature Methods 9, 72-74 (2012).

Knight, et al. Subtle chromosomal rearrangements in children with unexplained mental retardation. Lancet. Nov. 13, 1999;354(9191):1676-81.

Korlach, et al., Methods in Enzymology, Real-Time DNA Sequencing from Single Polymerase Molecules, (2010) 472:431-455.

Lee et al., "ACT-PRESTO: Rapid and consistent tissue clearing and labeling method for 3-dimensional (3D) imaging," Sci Rep., Jan. 11, 2016 doi: 10.1038/srep18631.

Lee et al., "Highly Multiplexed Subcellular RNA Sequencing in Situ," Science, Author Manuscript, Sep. 21, 2014, col. 343, pp. 1-12.

(56) References Cited

OTHER PUBLICATIONS

Li, et al. A single-cell-based platform for copy number variation profiling through digital counting of amplified genomic DNA fragments. ACS Appl Mater Interfaces. Mar. 24, 2017. doi:10.1021/acsami.7b03146. [Epub ahead of print].
Lupski. Genomic rearrangements and sporadic disease. Nat Genet. Jul. 2007;39(7 Suppl):S43-7.
Miller, J.C. et al. An improved zinc-finger nuclease architecture for highly specific genome editing. Nat. Biotechnol. 2007;25:778-785.
Nagano et al. "Single cell Hi-C reveals cell-to-cell variability in chromosome structure," Nature, vol. 502, No. 7469, Sep. 25, 2013.
Nextera Enrichment Sample Preparation Guide from Illumina, pp. 1-69 (Feb. 2013).
Oligotex Handbook. For purification of poly A+ RNA from total RNA and directly from cultured cells or tissues as well as purification of polyadenylated in vitro transcripts. Jun. 2012.
Pinto, et al. Functional impact of global rare copy No. variation in autism spectrum disorders. Nature. Jul. 15, 2010;466(7304):368-72. doi: 10.1038/nature09146. Epub Jun. 9, 2010.
Porteus, M.H., Baltimore D. Chimeric nucleases stimulate gene targeting in human cells. Science. 2003;300:763.
Ramskold et al. "Full-length mRNA-Seq from single-cell levels of RNA and individual circulating tumor cells" Nature Biotech (2012) 30(8)777-782.
Ran, et al., Genome Engineering Using the CRISPR-Cas9 System, Nature Protocol, (2013), 8(11):2281-2308.
Ropers. New perspectives for the elucidation of genetic disorders. Am J Hum Genet. Aug. 2007;81(2):199-207. Epub Jun. 29, 2007.
Rotem, A. et al. "Single-cell ChIP-seq reveals cell subpopulations defined by chromatin state" Nature Biotech (Oct. 12, 2015) 33(11):1165-1172.
Sander JD, et al. Selection-free zinc-finger-nuclease engineering by context-dependent assembly (CoDA). Nat. Methods. 2011;8:67-69.
Sebat, et al. Strong association of de novo copy No. mutations with autism. Science. Apr. 20, 2007;316(5823):445-9. Epub Mar. 15, 2007.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008; 105(32):11264-9. doi: 10.1073/pnas.0802970105. Epub Aug. 6, 2008.
Sigma, Straptavidin-agarose (S1638) product information sheet, (2007) www.sigma-aldrich.com.
Stoeckius, et al. "Large-scale simultaneous measurement of epitopes and transcriptomes in single cells." bioRxiv 113068; doi: https://doi.org/10.1101/113068.
Susaki et al., "Whole-Brain Imaging with Single-Cell Resolution Using Chemical Cocktails and Computational Analysis," Cell 157, 726-739 (2014).
Tomer et al., "Advanced CLARITY for rapid and high-resolution imaging of intact tissues," Nature Protocols 9, p. 1682-1697 (2014) doi:10.1038/nprot.2014.123.
Wang, et al. Digital karyotyping. Proc Natl Acad Sci U S A. Dec. 10, 2002;99(25):16156-61. Epub Dec. 2, 2002.
Wesolowska et al., "Cost-effective multiplexing before capture allows screening 25 000 clinically relevant SNPs in childhood acute lymphoblastic leukemia," Leukemia, vol. 25, pp. 1001-1006 (2001).
Wood AJ, et al. Targeted genome editing across species using ZFNs and TALENs. Science. 2011;333:307.
Zhang F, et al. Efficient construction of sequence-specific TAL effectors for modulating mammalian transcription. Nat. Biotechnol. 2011;29:149-153.
Zheng, et al. Massively parallel digital transcriptional profiling of single cells. Nat Commun. Jan. 16, 2017;8:14049. doi: 10.1038/ncomms14049.
Zhu et al. Hydrogel Droplet Microfluidics for High-Throughput Single Molecule/Cell Analysis. Accounts of Chemical Research Article ASAP. DOI: 10.1021 /acs.accounts.6b00370.

Hosokawa, M. et al. "Massively parallel whole genome amplification for single-cell sequencing using droplet microfluidics" Scientific Reports (2017) 7:5199 (11 pages).
Hosono, S. et al. "Unbiased whole-genomeamplification directly from clinical samples" Genome Res. May 2003; 13(5):954-64. Epub Apr. 14, 2003.
Imburgio, et al., "Studies of promoter recognition and start site selection by T7 RNA polymerase using a comprehensive collection of promoter variants", Biochemistry., 39:10419-30, 2000.
Kamperman, T. et al. "Centering Single Cells in Microgels via Delayed Crosslinking Supports Long-Term 3D Culture by Preventing Cell Escape" Small. Jun. 2017;13(22). doi: 10.1002/smll.201603711. Epub Apr. 28, 2017.
Katsura, S. et al. "Indirect micromanipulation of single molecules in water-in-oil emulsion" Electrophoresis (2001) 22(2):289-293.
Kenis, P.J. et al. "Microfabrication inside capillaries using multiphase laminar flow patterning" Science (Jul. 2, 1999);285(5424):83-85.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kozarewa, et al., "96-plex molecular barcoding for the Illumina Genome Analyzer", Methods Mol Biol., 733:279-98, 2011.
Kozarewa, L. et al. "Amplification-free Illumina sequencing-library preparation facilitates improved mapping and assembly of GC-biased genomes", Nat Methods., 6: 291-5, 2009.
Kwok et al., "Single-molecule analysis for molecular haplotyping", Hum Mutat., 23:442-6, 2004.
Lagally, E.T. et al. "Single-Molecule DNA Amplification and Analysis in an Integrated Microfluidic Device" Anal. Chem. (2001) 73(3):565-570.
Laird et al., Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material Nat Biotechnol. May 29, 2017. doi: 10.1038/nbt 3880 [Epub ahead of print].
Lennon et al. "A scalable, fully automated process for construction of sequence-ready barcoded libraries for 454." Genome Biology 11:R15 (201 O).
Lienemann, P.S. et al. "Single cell-laden protease-sensitive microniches for long-term culture in 3D" LabChip (2017) 17(4):727-737.
Linch, et al. Bone marrow processing and cryopreservation. Journal of Clinical Pathology; Feb. 1982, vol. 35, No. 2; pp. 186-190.
Lo, et al. On the design of clone-based haplotyping. Genome Biol. 2013;14(9):R100.
Lundin, et al., "Hierarchical molecular tagging to resolve long continuous sequences by massively parallel sequencing", Sci Rep., 3:1186, 2003.
MacAulay, et al. Single-Cell Multiomics: Multiple Measurements from Single Cells. Trends in Genetics 33.2 (2017): 155-168. PMC. Web. Dec. 18, 2017.
MacAulay; et al., "G&T-seq: parallel sequencing of single-cell genomes and transcriptomes." Nature Methods, 2015, p. 1-7.
Man, P. "Monolithic structures for integrated microfluidic analysis" (2001) Dissertation.
Maricic, T. et al. "Optimization of 454 sequencing library preparation from small amounts of DNA permits sequence determination of both DNA strands" Biotechniques. Jan. 2009; 46(1 ):51-2, 54-7.
MiRNA (http://www.exiqon.com/what-are-microRNAs) accessed Oct. 19, 2017 (Year: 2017).
Myllykangas et al., Targeted Sequencing Library Preparation By Genomic DNA Circularization, BMC Biotechnology, 2011, 11(122), 1-12.
Nisisako, T. et al. "Droplet formation in a microchannel network" Lab on a Chip (2002) 2:24-26.
Nisisako, T. et al. "Droplet Formation in a Microchannel on PMMA Plate" Abstract.

(56) References Cited

OTHER PUBLICATIONS

Orakdogen, N. "Novel responsive poly(N,N-dimethylaminoethyl methacrylate) gel beads: preparation, mechanical properties and pH-dependent swelling behavior" J Polym Res (2012) 19:9914 (Year: 2012).
Oyola, et al., "Optimizing Illumina next-generation sequencing library preparation for extremely AT-biased genomes", BMC Genomics., 13:1, 2012.
PCT/IB2010/002243, International Search Report and Written Opinion, dated Feb. 9, 2011, 13pgs.
Perrott, Jimmy. Optimization and Improvement of Emulsion PCR for the Ion Torrent Next-Generation Sequencing Platform (2011) Thesis.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
Rakszewska, A. et al. "One drop at a time: toward droplet microfluidics as a versatile tool for single-cell analysis" NPG Asia Materials (2014) 6(10):e133 (12 pages).
Ramsey, J.M. "The burgeoning power of the shrinking laboratory" Nature Biotech (1999) 17:1061-1062.
Reis, A. et al. "CRISPR/Cas9 and Targeted Genome Editing: A New Era in Molecular Biology" (2014) XP002766825: URL:https://ww. neb.com/tools-and-resources/feabture-articles/crispr-cas9-and-targeted-genome-editing-a-new-era-in-molecular-biology.
Reisner, et al., "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Roche "Using Multiplex Identifier (MID) Adaptors for the GS FLX Titanium Chemistry Basic MID Set" Genome Sequencer FLX System, Technnical Bulletin 004-2009, (Apr. 1, 2009) pp. 1-7. URL:http://454.com/downloads/my454/documentation/technical-bulletins/TCB-09004 UsingMultiplexIdentifierAdaptorsForTheGSFLXTitaniumSeriesChemistry-BasicMIDSet.pdf.
Roche "Using Multiplex Identifier (MID) Adaptors for the GS FLX Titanium Chemistry Extended MID Set" Genome Sequencer FLX System, Technnical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.
Rodrigue, S. et al. "Whole Genome Amplification and De novo Assembly of Single Bacterial Cells" PLoS ONE, (2009) 4(9):1-10.
Schubert, et al. "Microemulsifying fluorinated oils with mixtures of fluorinated an hydrogenated surfactants" Colloids and Surfaces A: Physicochemical and Engineering Aspects (1994) 84:97-106.
Schwartz; et al., "Capturing native long-range contiguity by in situ library construction and optical sequencing", PNAS (Nov. 2012), 109(46)18749-18754.
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Skerra, A. "Phosphorothioate primers improve the amplification of DNA sequences by DNA polymerases with proofreading activity" Nucleic Acids Res. Jul. 25, 1992; 20(14):3551-4.
Song, H. et al. "Reactions in Droplets in Microfluidic Channels" Angew. Chem. Int. Ed. (2006) 45:7336-7356.
Stoeckius et al. "Simultaneous epitope and transcriptome measurement in single cells" Nature Methods (Jul. 31, 2017) Supplemental Materials.
Syed, F. et al. Nature Methods (Nov. 2009) 2 pages.
Tewhey et al., Supplementary Materials, Nature Biotechnology, 2009, 27(11), 1-22.
Co-Pending U.S. Appl. No. 15/933,299, filed Mar. 22, 2018.
Co-Pending U.S. Appl. No. 15/975,468, filed May 9, 2018.
Co-Pending U.S. Appl. No. 15/980,473, filed May 15, 2018.
Co-Pending U.S. Appl. No. 15/985,388, filed May 21, 2018.
Depristo, M.A. et al. "A framework for variation discovery and genotyping using next-generation DNA sequencing data" Nature Genetics (2011) 43(5):491-498.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Lander, et al. Initial sequencing and analysis of the human genome. Nature, 409 (Feb. 15, 2001): 860-921.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Shaikh, et al. A modular microfluidic architecture for integrated biochemical analysis. Proc Natl Acad Sci U S A. Jul. 12, 2005;102(28):9745-50. Epub Jun. 28, 2005.
Wong, et al. "Multiplexed Barcoded CRISPR-Cas9 Screening Enabled by CombiGEM" PNAS (2016) 113:2544-2549.
Zhang, et al. One-step fabrication of supramolecular microcapsules from microfluidic droplets. Science. Feb. 10, 2012;335(6069):690-4. doi: 10.1126/science.1215416.
Adey, et al., "Ultra-low-input, tagmentation-based whole-genome bisulfite sequencing", Genome Research, 2012, 22 ;6): 1139-1143.
Anonymous: "TCEP=HCl" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCl_UG.pdf.
Ason et al. DNA sequence bias during Tn5 transposition. Journal of molecular biology 335.5 (2004): 1213-1225.
Bjornsson et al., Intra-individual change overtime in DNA methylation with familial clustering, JAMA, Jun. 25, 2008, vol. 299 No. 24, pp. 2877-2883.
Boyle, et al. "High-resolution genome-wide in vivo footprinting of diverse transcription factors in human cells", Genome Res. Mar. 2011;21(3):456-64.
Caruccio et al. "Nextera Technolgoy for NGS DNA Library Preparation: Simultaneous Fragmentation and Tagging by In Vitro Transposition" Nextera Technology, 2009 16-3, 1-3 (Year: 2009).
Co-Pending U.S. Appl. No. 16/000,803, filed Jun. 5, 2018.
Co-Pending U.S. Appl. No. 16/045,474, filed Jul. 25, 2018.
Co-Pending U.S. Appl. No. 16/052,431, filed Aug. 1, 2018.
Co-Pending U.S. Appl. No. 16/052,486, filed Aug. 1, 2018.
Co-Pending U.S. Appl. No. 16/056,231, filed Aug. 6, 2018.
Co-Pending U.S. Appl. No. 16/138,448, filed Sep. 21, 2018.
Co-Pending U.S. Appl. No. 16/144,832, filed Sep. 27, 2018.
EP14800805.5 Extended Search Report dated Jan. 23, 2017.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymerd-DNA Hybrid Hydrogel, Royal Soc. Chem. 7:1741-1746 (Dec. 20, 2010).
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Haring, et al. Chromatin immunoprecipitation: optimization, quantitative analysis and data normalization. Plant Methods. 2007; 3: 11.
Hu et al., Shape Controllable Microgel Particles Prepared by Microfluidic Combining External Crosslinking, Biomicrofluidics 6:26502 (May 18, 2012).
Joneja, A. et al. "Linear nicking endonuclease-mediated strand-displacement DNA amplification" Anal Biochem (2011) 414:58-69.

(56) References Cited

OTHER PUBLICATIONS

Knapp, M. et al. "Generating barcoded libraries for multiplex high-throughput sequencing" Methods Mol Biol (2012) 840:155-170 Epub Dec. 8, 2011.
Lai, H-H et al. "Characterization and use of laser-based lysis for cell analysis on-chip" J.R. Soc. Interface (2008) 5:S113-S121.
Lebedev, A. et al. "Hot Start PCR with heat-activatable primers: a novel approach for improved PCR performance" NAR (2008) 36(20):E131-1.
McGinnis, C.S. et al. "MULTI-seq: Scalable sample multiplexing for single-cell RNA sequencing using lipi-tagged indices" bioRxiv (2018) doi: http://dx.doi.org/10.1101/387241.
Park. ChIP-seq: advantages and challenges of a maturing technology. Nature Reviews Genetics vol. 10, pp. 669-680 (2009).
Savva et al. "The structural basis of specific base excision repair by uracil-DNA glycosylase" Nature (1995) 373:487-493.
Simon, et al., "Using formaldehyde-assisted isolation of regulatory elements (FAIRE) to isolate active regulatory DNA", Nature Protocols, 2012, 7(2): 256-267.
Smith, A.M. et al. "Highly-multiplexed barcode sequencing: an efficient method for parallel analysis of pooled samples" Nucl Acids Res (2010) 38(13):e142 Epub May 11, 2010.
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Zentner, et al. Surveying the epigenomic landscape, one base at a time. Genome Biol. Oct. 22, 2012;13(10):250. doi:10.1186/gb4051.
Co-Pending U.S. Appl. No. 16/107,685, filed Aug. 21, 2018.
Anonymous: "Dynal MPC(TM)-S", Oct. 13, 2008 (Oct. 13, 2008), XP055603532, Retrieved from the Internet: URL: https://www.veritastk.co.jp/products/pdf/120%2020D.Dynal_MPC-S(rev005).pdf [retrieved on Jul. 9, 2019].
Co-Pending U.S. Appl. No. 16/419.428, filed May 22, 2019.
Co-Pending U.S. Appl. No. 16/419,461, filed May 22, 2019.
Co-Pending U.S. Appl. No. 16/419,555, filed May 22, 2019.
Co-Pending U.S. Appl. No. 16/419,630, filed May 22, 2019.
Co-Pending U.S. Appl. No. 16/419,820, filed May 22, 2019.
Co-Pending U.S. Appl. No. 16/435,362, filed Jun. 7, 2019.
Co-Pending U.S. Appl. No. 16/435,417, filed Jun. 7, 2019.
Dhingra, et al. "A complete solution for high throughput single cell targeted multiomic DNA and RNA sequencing for cancer research." Poster. AACR 2019.
Ellison et al. "Mutations in Active-Site Residues of the Uracil-DNA Glycosytase Encoded by Vaccinia Virus are Incompatible with Virus Viability" J Virology (1996) 70(11):7965-7973.
Hamady, M. et al. "Error-correcting barcoded primers for pyrosequencing hundreds of samples in multiplex" Nature Methods (2008) 5(3):235-237.
Hamady, M. et al. "Error-correcting barcoded primers for pyrosequencing hundreds of samples in multiplex" Nature Methods (2008) 5(3):235-237, Supplementary Data pp. 1-34.
Schmieder, R. et al. "Fast Identification and Removal of Sequence Contamination from Genomic and Metagenomic Datasets" PLoS One (2011) 6(3): e17288. https://doi.org/10.1371/journal.pone.0017288.
Zhang, H. et al. "Massively Parallel Single-Molecule and Single-Cell Emulsion Reverse Transcription Polymerase Chain Reaction using Agarose Droplet Microfluidics" Anal Chem (2012) 84:3599-3606.
Zhang, H. et al. "Massively Parallel Single-Molecule and Single-Cell Emulsion Reverse Transcription Polymerase Chain Reaction using Agarose Droplet Microfluidics" Anal Chem (2012) 84:3599-3606, Supporting Information.
Changhua, et al., "Biochemistry and Molecular Biology Experiments and Technologies", Xi'an: Shaanxi Science and Technology Press, Apr. 30, 1994, pp. 209-210.
Chinese Office Action for Application No. 201680011692.7, dated Mar. 31, 2021, 32 pages including English language translation.
Kulkarni, et al., "Clinical Genomics", AP Elsevier, Nov. 14, 2014, pp. 302-305.

\* cited by examiner

METHODS AND COMPOSITIONS FOR TARGETED NUCLEIC ACID SEQUENCE COVERAGE

CROSS-REFERENCE TO RELATED APPLICATIONS

This application claims the benefit of U.S. Provisional Application No. 62/146,834, filed Apr. 13, 2015, and U.S. Provisional Application No. 62/119,996, filed Feb. 24, 2015, which are hereby incorporated by reference in their entirety for all purposes.

BACKGROUND OF THE INVENTION

Despite significant progress in sequencing technologies, about 5-10% of the human genome remains unassembled, unmapped, and poorly characterized. The reference assembly generally annotates these missing regions as multi-megabase heterochromatic gaps. This missing fraction of the genome includes structural features that remain resistant to accurate characterization using generally used sequencing technologies. De novo sequencing of the entire genome is not economically feasible, and thus there remains a need to reduce the costs associated with genome sequencing while retaining the benefits of genomic analysis on a large scale.

SUMMARY OF THE INVENTION

Accordingly, the present disclosure provides methods, systems and compositions for providing targeted coverage of selected regions of the genome to allow for de novo sequence assembly of those selected regions, and in some aspects, allow for combining that de novo coverage with re-sequencing of remaining regions of the genome with high throughput and high accuracy.

In some aspects, the present disclosure provides a method for sequencing one or more selected portions of a genome in which the method includes the steps of: (a) providing starting genomic material; (b) distributing individual nucleic acid molecules from the starting genomic material into discrete partitions such that each discrete partition contains an individual nucleic acid molecule; (c) amplifying selected portions of at least some of the individual nucleic acid molecules in the discrete partitions to form a population of amplicons; (d) barcoding the population of amplicons to form a plurality of barcoded fragments of the amplicons, wherein fragments within a given discrete partition each comprise a common barcode, thereby associating each fragment with the individual nucleic acid molecule from which it is derived; (e) obtaining sequence information from the plurality of fragments thereby sequencing one or more selected portions of a genome.

In further embodiments and in accordance with above, the one or more selected portions of the genome comprise highly polymorphic regions of the genome. In still further embodiments, the sequencing of the one or more selected portions of the genome is a de-novo sequencing.

In still further embodiments and in accordance with any of the above, the amplifying comprises PCR amplification across a region of at least 3.5 megabasepairs (Mb). In yet further embodiments, the amplifying comprises a PCR amplification utilizing multiple primer pairs staggered across a region of at least 3.0 Mb.

In some embodiments and in accordance with any of the above, the sequencing reaction is a short read, high accuracy sequencing reaction. In further embodiments, the sequence information generated in the obtaining step retains the molecular context of its originating individual nucleic acid.

In certain embodiments and in accordance with any of the above, prior to the obtaining step, the plurality of fragments is further enriched for fragments comprising at least a portion of the one or more selected portions of the genome by: (i) hybridizing probes complementary to regions in or near the one or more selected portions of the genome to the fragments to form probe-fragment complexes; (ii) capturing probe-fragment complexes to a surface of a solid support.

In some embodiments and in accordance with any of the above, the barcoded fragments of the amplicons within the discrete partitions represent about 100×-5000× coverage of the one or more selected portions of the genome. In further embodiments, the barcoded fragments of the amplicons within the discrete partitions represent about 200×-1000× coverage of the one or more selected portions of the genome. In still further embodiments, the barcoded fragments of the amplicons within the discrete partitions represent at least 1000× coverage of the one or more selected portions of the genome. In yet further embodiments, the barcoded fragments of the amplicons within the discrete partitions represent at least 2000× or 5000× coverage of the one or more selected portions of the genome.

In further aspects, the present disclosure provides a method of obtaining sequence information from one or more poorly characterized portions of a genomic sample, where the method includes the steps of: (a) providing individual first nucleic acid fragment molecules of the genomic sample in discrete partitions; (b) fragmenting the individual first nucleic acid fragment molecules within the discrete partitions to create a plurality of second fragments from each of the individual first nucleic acid fragment molecules; (c) amplifying selected regions of the plurality of second fragments that are poorly characterized to form a population of amplicons; (d) attaching a common barcode sequence to the amplicons within each discrete partition such that each of the amplicons is attributable to the discrete partition in which it is contained; (e) identifying sequences of the amplicons, thereby obtaining sequence information from one or more poorly characterized portions of the genomic sample.

In certain embodiments, and in accordance with any of the above, the amplifying comprises PCR amplification across a region of at least 3.5 megabasepairs (Mb). In further embodiments, the amplifying comprises a PCR amplification utilizing multiple primer pairs staggered across a region of at least 3.0 Mb. In still further embodiments, the multiple primer pairs contain uracils to prevent amplification of the primer sequences.

In some embodiments, and in accordance with any of the above, the identifying step preserves the molecular context of the sequences of the amplicons, such that the identifying further comprises identifying amplicons derived from the same individual first nucleic acid fragment molecules. In further embodiments, the method further comprises linking two or more of the individual first fragment molecules in an inferred contig based upon overlapping sequences of the plurality of second fragments, wherein the inferred contig comprises a length N50 of at least 10 kb.

In some embodiments, and in accordance with any of the above, the barcode sequence further comprises additional sequence segments. In further embodiments, additional sequence segments comprise one or more of a member selected from the group consisting of: primers, attachment sequences, random n-mer oligonucleotides, oligonucleotides comprising uracil nucleobases. In yet further embodiments, the barcode is selected from a library of at least 700,000 barcodes.

In some embodiments, and in accordance with any of the above, the genomic sample within each discrete partition comprises genomic DNA from a single cell. In further embodiments, each discrete partition comprises genomic DNA from a different chromosome.

In some embodiments, and in accordance with any of the above, the discrete partitions comprise droplets in an emulsion.

In some embodiments, and in accordance with any of the above, the barcoded amplicons within the discrete partitions represent about 1000×-5000× coverage of the one or more poorly characterized portions of the genome.

In further aspects, the present application provides a method for obtaining sequence information from one or more portions of a genomic sample while retaining molecular context, the method including the steps of: (a) providing starting genomic material; (b) distributing individual nucleic acid molecules from the starting genomic material into discrete partitions such that each discrete partition contains a first individual nucleic acid molecule; (c) providing a population enriched for fragments comprising at least a portion of the one or more selected portions of the genome; (d) attaching a common barcode sequence to the fragments within each discrete partition such that each of the fragments is attributable to the discrete partition in which it was contained; (e) obtaining sequence information from the fragments, thereby sequencing one or more targeted portions of the genomic sample while retaining molecular context.

In still further aspects, the present disclosure provides a method for obtaining sequence information from one or more portions of a genomic sample while retaining molecular context, the method including the steps of: (a) providing starting genomic material; (b) distributing individual nucleic acid molecules from the starting genomic material into discrete partitions such that each discrete partition contains a first individual nucleic acid molecule; (c) providing a population within at least some of the discrete partitions that is enriched for sequences of the fragments comprising at least a portion of the one or more selected portions of the genome; (d) attaching a common barcode sequence to the fragments within each discrete partition such that each of the fragments is attributable to the discrete partition in which it was contained; (e) separating discrete partitions containing fragments comprising at least a portion of the one or more selected portions of the genome from discrete partitions containing no fragments comprising the one or more selected portions of the genome; (f) obtaining sequence information from the fragments comprising at least a portion of the one or more selected portions of the genome, thereby sequencing one or more targeted portions of the genomic sample while retaining molecular context.

In further embodiments and in accordance with any of the above, the providing a population enriched for sequences of the fragments comprising at least a portion of the one or more selected portions of the genome comprises directed PCR amplification of the fragments comprising at least a portion of the one or more selected portions of the genome to produce a population of amplicons comprising at least a portion of the one or more selected portions of the genome. In still further embodiments, this providing step further comprises attaching a detectable label to the amplicons, which in some embodiments may include a fluorescent molecule. In yet further embodiments the step of separating discrete partitions containing fragments comprising at least a portion of the one or more selected portions of the genome from discrete partitions containing no fragments comprising the one or more selected portions of the genome includes sorting the partitions emitting a signal from the detectable labels from the partitions without such a signal.

In some embodiments and in accordance with any of the above, prior to obtaining sequence information from the fragments, the discrete partitions are combined and the fragments are pooled together. In further embodiments, the step of obtaining sequence information from the fragments is conducted in such a way as to maintain the molecular context of the sequences of the fragments, such that the identifying further comprises identifying fragments derived from the same first individual nucleic acid molecules. In still further embodiments, this obtaining of sequence information includes a sequencing reaction selected from the group consisting of: short read-length sequencing reactions and long read-length sequencing reactions. In yet further embodiments, the sequencing reaction is a short read, high accuracy sequencing reaction.

In some embodiments and in accordance with any of the above, the discrete partitions comprise droplets in an emulsion. In further embodiments, the barcoded fragments within the discrete partitions represent about 100×-5000× coverage of the one or more selected portions of the genome. In still further embodiments, the barcoded fragments within the discrete partitions represent about 200×-1000× coverage of the one or more selected portions of the genome. In yet further embodiments, the barcoded fragments of the amplicons within the discrete partitions represent at least 1000× coverage of the one or more selected portions of the genome. In still further embodiments, the barcoded fragments within the discrete partitions represent at least 2000× or 5000× coverage of the one or more selected portions of the genome.

In some aspects and in accordance with any of the above, the present disclosure provides methods for obtaining sequence information from one or more portions of a genomic sample while retaining molecular context, including the steps of (a) providing genomic material; (b) separating individual nucleic acid molecules from the genomic material to form separated individual nucleic acid molecules; (c) providing a population enriched for fragments comprising at least a portion of the one or more selected portions of the genome from the separated individual nucleic acid molecules. In certain embodiments, the separating step is accomplished using any method that allows for one or more nucleic acid molecules to be sorted and processed in relative isolation from other one or more nucleic acid molecules. In some embodiments, the separating is a physical separation into different compartments on a substrate or into distinct partitions. In further embodiments, at least a plurality of the fragments are attributable to the individual nucleic acid molecules from which they are derived. That attribution is obtained using any methods that allow designation of a particular fragment as originating with a particular individual nucleic acid molecule. In certain exemplary embodiments, that attribution is obtained by barcoding fragments. In further aspects, sequence information is obtained from the fragments, thereby sequencing one or more targeted portions of the genomic sample while retaining molecular context.

DETAILED DESCRIPTION OF THE INVENTION

Figure 1:
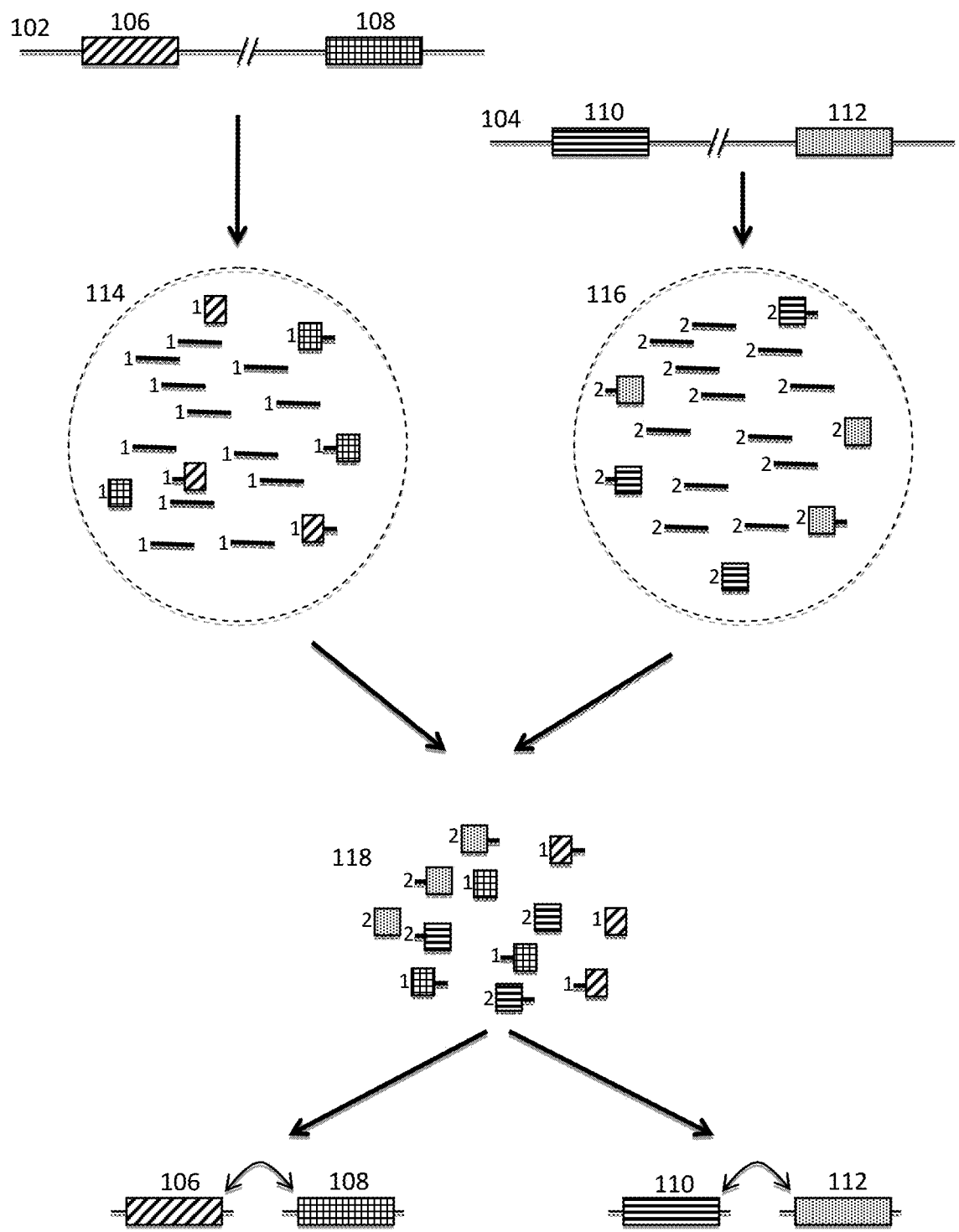
FIG. 1 provides a schematic illustration of identification and analysis of targeted genomic regions using conventional processes versus the processes and systems described herein.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) Biochemistry (4th Ed.) Freeman, New York, Gait, *"Oligonucleotide Synthesis: A Practical Approach"* 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

I. Overview

This disclosure provides methods, compositions and systems useful for characterization of genetic material. In particular, the methods, compositions and systems described herein provide increased and redundant coverage of selected portions of the genome such that additional redundant sequence information can be obtained from those selected portion of the genome. In specific instances, that additional sequence information provides enough information to allow for de novo sequencing of those selected portions of the genome.

In general, the methods, compositions, and systems described herein provide genetic characterization of selected regions of a genome. This genetic characterization is of sufficient depth to allow de novo sequencing of the selected regions of the genome. This de novo sequencing is of particular use for regions of the genome that are poorly characterized, are highly polymorphic, and/or diverge from reference sequences. As will be appreciated, a significant percentage (at least 5-10% according to, for example Altemose et al., PLOS Computational Biology, May 15, 2014, Vol. 10, Issue 5) of the human genome remains unassembled, unmapped, and poorly characterized. The reference assembly generally annotates these missing regions as multi-megabase heterochromatic gaps, found primarily near centromeres and on the short arms of the acrocentric chromosomes. This missing fraction of the genome includes structural features that remain resistant to accurate characterization using generally used sequencing technologies. Exemplary regions that are resistant to accurate characterization include areas that have close homologous pseudo-genes (for example SMN1/2 CYP2D6), areas that have substantial repeated sequences throughout the genome, including without limitation transposons (such as SINEs, LINEs), and particularly areas that have tremendous variation for which reference sequences serve as a poor guide (such as the regions encoding the genes for the human leukocyte antigen (HLA) complex). The methods, compositions, and systems described herein combine selective amplification of the regions of interest with the ability to maintain molecular context, thereby allowing for de novo sequencing of genomic regions that are generally poorly characterized, as well as optionally providing long range molecular context of these regions in the larger genome.

In specific instances, methods described herein include a step in which selected regions of the genome are selectively amplified prior to sequencing. This amplification, which is generally conducted using methods known in the art (including without limitation PCR amplification) provides at least 1×, 10×, 20×, 50×, 100×, 200×, 500×, 1000×, 1500×, 2000×, 5000×, or 10000× coverage of the selected regions of the genome, thereby providing a quantity of nucleic acids to allow de novo sequencing of those selected regions. In further embodiments, the amplification provides at least 1×-20×, 50×-100×, 200×-1000×, 1500×-5000×, 5000×-10,000×, 1000×-10000×, 1500×-9000×, 2000×-8000×, 2500×-7000×, 3000×-6500×, 3500×-6000×, 4000×-5500× coverage of the selected regions of the genome.

The amplification is generally conducted through extension of primers complementary to sequences within or near the selected regions of the genome. In some cases, a library of primers is used that is designed to tile across the regions of interest—in other words, the library of primers is designed to amplify regions at specific distances along the selected regions of the genome. In some instances, the selective amplification utilizes primers that are complementary to every 10, 15, 20, 25, 50, 100, 200, 250, 500, 750, 1000, or 10000 bases along the selected regions of the genome. In still further examples, the tiled library of primers is designed to capture a mixture of distances—that mixture can be a random mixture of distances or intelligently designed such that specific portions or percentages of the selected regions are amplified by different primer pairs.

In general, the methods and systems described herein accomplish targeted genomic sequencing by providing for the determination of the sequence of selected regions of the genome, and this sequencing information is obtained using methods that have the advantages of the extremely low sequencing error rates and high throughput of short read sequencing technologies.

Sequencing of nucleic acids is typically carried out in a manner that preserves the molecular context of sequence reads or portions of sequence reads. By that is meant that multiple sequence reads or multiple portions of sequence reads may be attributable to a single originating molecule of a nucleic acid. By 'attributable to' is meant that the sequence reads can be identified as falling within the linear sequence of bases of their particular originating molecules of a nucleic acid—in other words, if fragments 1 and 2 are generated from originating nucleic acid molecule A, then the sequencing is carried out in a manner such that sequence reads from fragments 1, 2, 3 and 4 retain their molecular context and it is readily ascertained that fragments 1 and 2 are derived from originating molecule A.

While this single molecule of a nucleic acid may be of any of a variety of lengths, in preferred aspects, it will be a relatively long molecule, allowing for preservation of long range molecular context. In particular, the single originating molecule is preferably substantially longer than the typical short read sequence length, e.g., longer than 200 bases, and is often at least 1000 bases or longer, 5000 bases or longer, 10,000 bases or longer, 20,000 bases or longer, 30,000 bases or longer, 40,000 bases or longer, 50,000 bases or longer, 60,000 bases or longer, 70,000 bases or longer, 80,000 bases or longer, 90,000 bases or longer, or 100,000 bases or longer, and in some cases up to 1 megabase or longer.

In general, as shown in FIG. 1, the methods and systems described herein may be used to characterize nucleic acids, particularly nucleic acids from selected regions of the genome, while retaining molecular context. As shown, two discrete individual nucleic acids 102 and 104 are illustrated, each having a number of regions of interest, e.g., region 106 and 108 in nucleic acid 102, and regions 110 and 112 in nucleic acid 104. The regions of interest in each nucleic acid are linked within (e.g., originate from) the same nucleic acid molecule, but in some cases these regions may be relatively separated from each other, e.g., more than 1 kb apart, more than 5 kb apart, more than 10 kb apart, more than 20 kb apart, more than 30 kb apart, more than 40 kb apart, more than 50 kb apart, and in some cases, as much as 100 kb apart or more. The regions of interest are generally discrete and separate parts of the genome—in some cases, such regions are poorly characterized regions. The regions of interest may also denote individual genes, gene groups, exons. As shown, each nucleic acid 102 and 104 is separated. As illustrated in FIG. 1, each nucleic acid is separated into its own partition 114 and 116, respectively; however, as will be appreciated, the methods described herein are not limited to the use of such partitions and any method of separating of nucleic acid molecules can be used and then those separated nucleic acid molecules can be further processed in accordance with any of the methods disclosed herein. As noted elsewhere herein, partitions such as 114 and 116 in FIG. 1 are, in many cases, aqueous droplets in a water in oil emulsion. Within each droplet, portions of each fragment are copied in a manner that preserves the original molecular context of those fragments, e.g., as having originated from the same molecule. Such molecular context can be preserved using any method that allows for attribution of the fragment to the original nucleic acid molecule from which it was derived. As shown in FIG. 1, one method by which this is achieved is through the inclusion in each copied fragment of a barcode sequence, e.g., barcode sequence "1" or "2" as illustrated, that is representative of the droplet into which the originating fragment was partitioned. For whole genome sequence analysis applications, one could simply pool all of the copied fragments and their associated barcodes, in order to sequence and reassemble the full range sequence information from each of the originating nucleic acids 102 and 104. However, in many cases, it is more desirable to only analyze specific targeted portions of the overall genome, in order to provide greater focus on scientifically relevant portions of the genome, and to minimize the time and expense of performing sequencing on less relevant or irrelevant portions of the genome. Other sequencing methods that assist in preserving molecular context include single molecule sequencing processes, such as SMRT sequencing available from Pacific Biosciences, and nanopore sequencing described by, e.g., Oxford Nanopore, and Truseq SLR processes available from Illumina, Inc.

In accordance with the above, in addition to the barcoding step, there may be one or more steps of selective amplification, such that if nucleic acids 102 or 104 contain selected genomic regions of interest, amplicons from those regions will form a larger percentage of the fragments in each of the partitions 114 and 116. This amplification step will generally take place prior to or simultaneously with the attachment of the barcodes in accordance with the methods described herein, although in some embodiments the amplification step may also occur subsequent to attachment of the barcodes.

Because the pooled fragments within library 118 retain their original molecular context, e.g., through the retention of the barcode information, they may be reassembled into their original molecular contexts with embedded (at times, long range) linkage information, e.g., with inferred linkage as between each of the assembled regions of interest 106:108 and 110:112. By way of example, one may identify direct molecular linkage between two disparate targeted portions of the genome, e.g., two or more exons, and that direct molecular linkage may be used to identify structural variations and other genomic characteristics. For situations in which selective amplification is utilized to increase the amount of nucleic acid fragments containing portions of selected regions of the genome, then the ability to identify the molecular context also provides a way to sequence those selected regions of the genome, often at a depth of coverage that allows for de novo assembly of those regions.

In certain situations, sequencing methods described herein include a combination of deep coverage of the selected regions with lower level linked reads across longer ranges of the genome. As will be appreciated, this combination of de novo and re-sequencing provides an efficient way to sequence an entire genome and/or large portions of a genome. Targeted coverage of poorly characterized and/or highly polymorphic regions through the selective amplification methods described herein provides the amount of nucleic acid material at a coverage level necessary for de novo sequence assembly of those regions, whereas linked genomic sequencing over other regions of the genome allows for high throughput analysis of the remainder of the genome by providing sequence information as to discrete regions which are linked together through preservation of their molecular context. The methods and compositions described herein are uniquely amenable to allowing for a combination of de novo and linked read sequencing, because the same sequencing platform and sequencing library can be used for both types of coverage. The population of nucleic acids and/or nucleic acid fragments that are sequenced in accordance with the methods described herein contain sequences from both the genomic regions for de novo sequencing and the genomic regions for re-sequencing—the proportion of nucleic acids covering the regions of interest for de novo sequencing is higher than the nucleic acids covering the other regions of the genome due to the targeted amplification methods described in further detail herein. Such methods are further amenable for de novo assembly of haplotypes, because the methods described herein allow phase information to be retained during assembly.

In addition to providing the ability to obtain sequence information from selected regions of the genome, the methods and systems described herein can also provide other characterizations of genomic material, including without limitation haplotype phasing, identification of structural variations, and identifying copy number variations, as described in U.S. patent application Ser. Nos. 14/752,589 and 14/752,602, which are herein incorporated by reference in their entirety for all purposes and in particular for all written description, figures and working examples directed to characterization of genomic material.

Methods of processing and sequencing nucleic acids in accordance with the methods and systems described in the present application are also described in further detail in U.S. patent application Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material.

Figure 2:
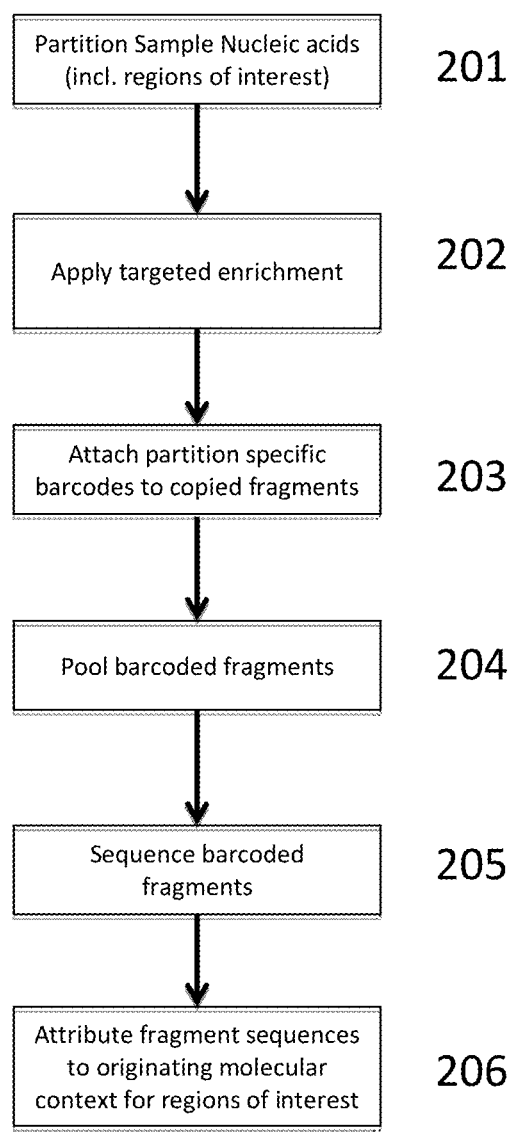
FIG. 2 provides schematic illustration of identification and analysis of targeted genomic regions using processes and systems described herein.

Generally, methods of the invention include steps as illustrated in FIG. 2, which provides a schematic overview of methods of the invention discussed in further detail herein. As will be appreciated, the method outlined in FIG. 2 is an exemplary embodiment that may be altered or modified as needed and as described herein.

As shown in FIG. 2, the methods described herein will in most examples include a step in which sample nucleic acids containing the targeted regions of interest are separated, for example into partitions (201). Generally, each partition containing nucleic acids from genomic regions of interest will undergo a targeted enrichment to produce a population of fragments in which a large proportion will contain sequences from a selected genomic region (202). Those fragments are then further fragmented or copied in such a way as to preserve the original molecular context of the fragments (203), usually by barcoding the fragments that are specific to the partition in which they are contained, although any other methods of attributing the original molecular context of the fragments can be used. Each partition may in some examples include more than one nucleic acid, and will in some instances contain several hundred nucleic acid molecules—in situations in which multiple nucleic acids are within a partition, any particular locus of the genome will generally be represented by a single individual nucleic acid prior to barcoding. The barcoded fragments of step 203 can be generated using any methods known in the art—in some examples, oligonucleotides are the samples within the distinct partitions. Such oligonucleotides may comprise random sequences intended to randomly prime numerous different regions of the samples, or they may comprise a specific primer sequence targeted to prime upstream of a targeted region of the sample. In further examples, these oligonucleotides also contain a barcode sequence, such that the replication process also barcodes the resultant replicated fragment of the original sample nucleic acid. Such barcodes can be added using any method known in the art, including addition of barcode sequences during amplification methods that amplify segments of the individual nucleic acid molecules as well as insertion of barcodes into the original individual nucleic acid molecules using transposons, including methods such as those described in Amini et al., Nature Genetics 46: 1343-1349 (2014) (advance online publication on Oct. 29, 2014). A particularly elegant process for use of these barcode oligonucleotides in amplifying and barcoding samples is described in detail in U.S. patent application Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material. Extension reaction reagents, e.g., DNA polymerase, nucleoside triphosphates, co-factors (e.g., $Mg^{2+}$ or $Mn^{2+}$ etc.), that are also contained in the partitions, then extend the primer sequence using the sample as a template, to produce a complementary fragment to the strand of the template to which the primer annealed, and the complementary fragment includes the oligonucleotide and its associated barcode sequence. Annealing and extension of multiple primers to different portions of the sample can result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In further examples, this replication process is configured such that when the first complement is duplicated, it produces two complementary sequences at or near its termini to allow the formation of a hairpin structure or partial hairpin structure, which reduces the ability of the molecule to be the basis for producing further iterative copies.

Returning to the method exemplified in FIG. 2, once the partition-specific barcodes are attached to the copied fragments, the barcoded fragments are then pooled (204). The pooled fragments are then sequenced (205) and the sequences of the fragments are attributed to their originating molecular context (206), such that the targeted regions of interest are both identified and also linked with that originating molecular context. An advantage of the methods and systems described herein is that attaching a partition- or sample-specific barcode to the copied fragments prior to enriching the fragments for targeted genomic regions preserves the original molecular context of those targeted regions, allowing them to be attributed to their original partition and thus their originating sample nucleic acid molecule.

In addition to the above workflow, targeted genomic regions may be further enriched, isolated or separated, i.e., "pulled down," for further analysis, particularly sequencing, using methods that include both chip-based and solution-based capture methods. Such methods utilize probes that are complementary to the genomic regions of interest or to regions near or adjacent to the genomic regions of interest. For example, in hybrid (or chip-based) capture, microarrays containing capture probes (usually single-stranded oligonucleotides) with sequences that taken together cover the region of interest are fixed to a surface. Genomic DNA is fragmented and may further undergo processing such as end-repair to produce blunt ends and/or addition of additional features such as universal priming sequences. These fragments are hybridized to the probes on the microarray. Unhybridized fragments are washed away and the desired fragments are eluted or otherwise processed on the surface for sequencing or other analysis, and thus the population of fragments remaining on the surface is enriched for fragments containing the targeted regions of interest (e.g., the regions comprising the sequences complementary to those contained in the capture probes). The enriched population of fragments may further be amplified using any amplification technologies known in the art. Exemplary methods for such targeted pull down enrichment methods are described in U.S. patent application Ser. No. 14/927,297, filed on Oct. 29, 2015, which is hereby incorporated by reference in its entirety for all purposes and in particular for all teachings related to targeted pull down enrichment methods and sequencing methods, including all written description, figures and examples.

As noted above, the methods and systems described herein provide individual molecular context for short sequence reads of longer nucleic acids. Such individual molecular context can be provided by any method or composition that allows attribution of the shorter sequence reads to the originating individual nucleic acid. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. As will be appreciated, by providing long range individual molecular context, one can also derive the phasing information of variants within that individual molecular context, e.g., variants on a particular long molecule will be, by definition commonly phased.

By providing longer range individual molecular context, the methods and systems of the invention also provide much longer inferred molecular context (also referred to herein as a "long virtual single molecule read"). Sequence context, as described herein, can include mapping or providing linkage of fragments across different (generally on the kilobase scale) ranges of full genomic sequence. These methods include mapping the short sequence reads to the individual longer molecules or contigs of linked molecules, as well as long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

Furthermore, while one may utilize the long range sequence context associated with long individual molecules, having such long range sequence context also allows one to infer even longer range sequence context. By way of one example, by providing the long range molecular context described above, one can identify overlapping variant portions, e.g., phased variants, translocated sequences, etc., among long sequences from different originating molecules, allowing the inferred linkage between those molecules. Such inferred linkages or molecular contexts are referred to herein as "inferred contigs". In some cases when discussed in the context of phased sequences, the inferred contigs may represent commonly phased sequences, e.g., where by virtue of overlapping phased variants, one can infer a phased contig of substantially greater length than the individual originating molecules. These phased contigs are referred to herein as "phase blocks".

By starting with longer single molecule reads (e.g., the "long virtual single molecule reads" discussed above), one can derive longer inferred contigs or phase blocks than would otherwise be attainable using short read sequencing technologies or other approaches to phased sequencing. See, e.g., published U.S. Patent Application No. 2013-0157870. In particular, using the methods and systems described herein, one can obtain inferred contig or phase block lengths having an N50 (where the sum of the block lengths that are greater than the stated N50 number is 50% of the sum of all block lengths) of at least about 10 kb, at least about 20 kb, at least about 50 kb. In more preferred aspects, inferred contig or phase block lengths having an N50 of at least about 100 kb, at least about 150 kb, at least about 200 kb, and in many cases, at least about 250 kb, at least about 300 kb, at least about 350 kb, at least about 400 kb, and in some cases, at least about 500 kb or more, are attained. In still other cases, maximum phase block lengths in excess of 200 kb, in excess of 300 kb, in excess of 400 kb, in excess of 500 kb, in excess of 1 Mb, or even in excess of 2 Mb may be obtained.

In one aspect, and in conjunction with any of the capture methods described above and later herein, the methods and systems described herein provide for the separation of sample nucleic acids for further processing in accordance with any of the methods described herein. Such separation can be of any form that allows the nucleic acids to undergo further processing and reactions in relative isolation from other nucleic acids from which they are separated. The separating can be in terms of single nucleic acids each separated from all other nucleic acids, or into groups of two or more nucleic acids, which are then separated from other groups of nucleic acids. In some exemplary embodiments, such separating includes compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers or other means of attribution (in some examples, barcodes), may be previously, subsequently or concurrently delivered to the separated nucleic acids in order to allow for the later attribution of the characteristics, e.g., nucleic acid sequence information, to the sample nucleic acids from which that information is derived. In certain exemplary embodiments in which the nucleic acids are separated into compartments or partitions, the identifier can be included within or introduced to a particular compartment, and particularly to relatively long stretches of contiguous sample nucleic acids that may be originally deposited into the partitions.

The sample nucleic acids utilized in the methods described herein typically represent a number of overlapping portions of the overall sample to be analyzed, e.g., an entire chromosome, exome, or other large genomic portion. These sample nucleic acids may include whole genomes, individual chromosomes, exomes, amplicons, or any of a variety of different nucleic acids of interest. The sample nucleic acids are typically partitioned such that the nucleic acids are present in the partitions in relatively long fragments or stretches of contiguous nucleic acid molecules. Typically, these fragments of the sample nucleic acids may be longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range molecular context described above.

The sample nucleic acids are also typically partitioned at a level whereby a given partition has a very low probability of including two overlapping fragments of a genomic locus. This is typically accomplished by providing the sample nucleic acid at a low input amount and/or concentration during the partitioning process. As a result, in preferred cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Published Application No. 2013-0079231 and 2013-0157870) typically only operate with a hundred to a few hundred different barcode sequences, and employ a limiting dilution process of their sample in order to be able to attribute barcodes to different cells/nucleic acids. As such, they will generally operate with far fewer than 100 cells, which would typically provide a ratio of genomes:(barcode type) on the order of 1:10, and certainly well above 1:100. The systems described herein, on the other hand, because of the high level of barcode diversity, e.g., in excess of 10,000, 100,000, 500,000, etc. diverse barcode types, can operate at genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

Often, the sample is combined with a set of oligonucleotide tags that are releasably-attached to beads prior to the partitioning step. Methods for barcoding nucleic acids are known in the art and described herein. In some examples, methods are utilized as described in Amini et al, 2014, Nature Genetics, Advance Online Publication), which is herein incorporated by reference in its entirety for all purposes and in particular for all teachings related to attaching barcodes or other oligonucleotide tags to nucleic acids. In further examples, the oligonucleotides may comprise at least a first and second region. The first region may be a barcode region that, as between oligonucleotides within a given partition, may be substantially the same barcode sequence, but as between different partitions, may and, in most cases is a different barcode sequence. The second region may be an N-mer (either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, e.g., an exome or other targeted region. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn, as can analyses across long ranges of genomic sequence—for example, identification of sequence information across stretches of poorly characterized regions of the genome. Such information may also be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Ensemble sample preparation and sequencing methods are predisposed towards primarily identifying and characterizing the majority constituents in the sample, and are not designed to identify and characterize minority constituents, e.g., genetic material contributed by one chromosome, from a poorly characterized or highly polymorphic region of the genome, or material from one or a few cells, or fragmented tumor cell DNA molecule circulating in the bloodstream, that constitute a small percentage of the total DNA in the extracted sample. The methods described herein include selective amplification methods that increase the genetic material from these minority constituents, and the ability to retain the molecular context of this genetic material further provides genetic characterization of these constituents. The described methods and systems also provide a significant advantage for detecting populations that are present within a larger sample. As such, they are particularly useful for assessing haplotype and copy number variations—the methods disclosed herein are also useful for providing sequence information over regions of the genome that are poorly characterized or are poorly represented in a population of nucleic acid targets due to biases introduced during sample preparation.

The use of the barcoding technique disclosed herein confers the unique capability of providing individual molecular context for a given set of genetic markers, i.e., attributing a given set of genetic markers (as opposed to a single marker) to individual sample nucleic acid molecules, and through variant coordinated assembly, to provide a broader or even longer range inferred individual molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

As described previously, an advantage of the methods and systems described herein is that they can achieve the desired results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, inc. (GAIIx, NextSeq, MiSeq, HiSeq, ×10), Ion Torrent division of Thermo-Fisher (Ion Proton and Ion PGM), pyrosequencing methods, as well as others.

Of particular advantage is that the methods and systems described herein utilize these short read sequencing technologies and do so with their associated low error rates and high throughputs. In particular, the methods and systems described herein achieve the desired individual molecular readlengths or context, as described above, but with individual sequencing reads, excluding mate pair extensions, that are shorter than 1000 bp, shorter than 500 bp, shorter than 300 bp, shorter than 200 bp, shorter than 150 by or even shorter; and with sequencing error rates for such individual molecular readlengths that are less than 5%, less than 1%, less than 0.5%, less than 0.1%, less than 0.05%, less than 0.01%, less than 0.005%, or even less than 0.001%.

II. Work Flow Overview

The methods and systems described in the disclosure provide for separating nucleic acids into different groups or into different regions such that the separated nucleic acids can undergo further processing and/or reactions in relative isolation from one or more other nucleic acids. Such separating can in certain exemplary instances include depositing or partitioning individual samples (e.g., nucleic acids) into discrete partitions, where each partition maintains separation of its own contents from the contents in other partitions. As used herein, the partitions refer to containers or vessels that may include a variety of different forms, e.g., wells, tubes, micro or nanowells, through holes, or the like. In preferred aspects, however, the partitions are flowable within fluid streams. These vessels may be comprised of, e.g., microcapsules or micro-vesicles that have an outer barrier surrounding an inner fluid center or core, or they may be a porous matrix that is capable of entraining and/or retaining materials within its matrix. In preferred aspect, however, these partitions may comprise droplets of aqueous fluid within a non-aqueous continuous phase, e.g., an oil phase. A variety of different vessels are described in, for example, U.S. patent application Ser. No. 13/966,150, filed Aug. 13, 2013. Likewise, emulsion systems for creating stable droplets in non-aqueous or oil continuous phases are described in detail in, e.g., Published U.S. Patent Application No. 2010-0105112. In certain cases, microfluidic channel networks are particularly suited for generating partitions as described herein. Examples of such microfluidic devices include those described in detail in U.S. patent application Ser. No. 14/682,952, filed Apr. 9, 2015, the full disclosure of which is incorporated herein by reference in its entirety for all purposes. Alternative mechanisms may also be employed in the partitioning of individual cells, including porous membranes through which aqueous mixtures of cells are extruded into non-aqueous fluids. Such systems are generally available from, e.g., Nanomi, Inc.

In methods utilizing droplets in an emulsion, partitioning of sample materials, e.g., nucleic acids, into discrete partitions may generally be accomplished by flowing an aqueous, sample containing stream, into a junction into which is also flowing a non-aqueous stream of partitioning fluid, e.g., a fluorinated oil, such that aqueous droplets are created within the flowing stream partitioning fluid, where such droplets include the sample materials. As described below, the partitions, e.g., droplets, also typically include co-partitioned barcode oligonucleotides. The relative amount of sample materials within any particular partition may be adjusted by controlling a variety of different parameters of the system, including, for example, the concentration of sample in the aqueous stream, the flow rate of the aqueous stream and/or the non-aqueous stream, and the like. The partitions described herein are often characterized by having extremely small volumes. For example, in the case of droplet based partitions, the droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Where co-partitioned with beads, it will be appreciated that the sample fluid volume within the partitions may be less than 90% of the above described volumes, less than 80%, less than 70%, less than 60%, less than 50%, less than 40%, less than 30%, less than 20%, or even less than 10% the above described volumes. In some cases, the use of low reaction volume partitions is particularly advantageous in performing reactions with very small amounts of starting reagents, e.g., input nucleic acids. Methods and systems for analyzing samples with low input nucleic acids are presented in U.S. patent application Ser. Nos. 14/752,589 and 14/752,602, the full disclosure of which are hereby incorporated by reference in their entirety.

Once the samples are introduced into their respective partitions, in accordance with the methods and systems described herein, the sample nucleic acids within partitions are generally subjected to selective amplification, such that regions of the genome that are of interest for targeted coverage to allow for de novo sequencing are present in higher proportion in comparison to other regions of the genome (although, as will be appreciated, those other regions of the genome may also be amplified, but to a lesser extent, as they are not of interest for de novo coverage). In certain embodiments, the genomic regions of interest are amplified to provide at least 1×, 2×, 5×, 10×, 20×, 30×, 40× or 50× coverage of those selected regions of the genome. In further embodiments, all of the nucleic acids within a partition are amplified, but selected genomic regions are amplified in a targeted way such that at least 1-5, 2-10, 3-15, 4-20, 5-25, 6-30, 7-35, 8-40, 9-45, or 10-50 times more amplicons are produced from those selected genomic regions than from other parts of the genome.

Simultaneously with or subsequent to the selective amplification of selected regions of the genome, the nucleic acids (or fragments thereof) within the partitions are provided with unique identifiers such that, upon characterization of those nucleic acids they may be attributed as having been derived from their respective origins. Accordingly, the sample nucleic acids are typically co-partitioned with the unique identifiers. In some exemplary embodiments, such unique identifiers are barcode sequences. For the sake of clarity, much of the discussion herein is directed to identifiers comprising barcode sequences, but, as will be appreciated, any unique identifiers that can be used to retain molecular context for sequence reads can be used in accordance with the methods described herein. In some preferred aspects, the unique identifiers are provided in the form of oligonucleotides that comprise nucleic acid barcode sequences that may be attached to the nucleic acid samples. The oligonucleotides are partitioned such that as between oligonucleotides in a given partition, the nucleic acid barcode sequences contained therein are the same, but as between different partitions, the oligonucleotides can, and preferably have differing barcode sequences. In preferred aspects, only one nucleic acid barcode sequence will be associated with a given partition, although in some cases, two or more different barcode sequences may be present.

The nucleic acid barcode sequences will typically include from 6 to about 20 or more nucleotides within the sequence of the oligonucleotides. These nucleotides may be completely contiguous, i.e., in a single stretch of adjacent nucleotides, or they may be separated into two or more separate subsequences that are separated by one or more nucleotides. Typically, separated subsequences may typically be from about 4 to about 16 nucleotides in length.

The co-partitioned oligonucleotides also typically comprise other functional sequences useful in the processing of the partitioned nucleic acids. These sequences include, e.g., targeted or random/universal amplification primer sequences for amplifying the genomic DNA from the individual nucleic acids within the partitions while attaching the associated barcode sequences, sequencing primers, hybridization or probing sequences, e.g., for identification of presence of the sequences, or for pulling down barcoded nucleic acids, or any of a number of other potential functional sequences. Again, co-partitioning of oligonucleotides and associated barcodes and other functional sequences, along with sample materials is described in, for example, U.S. patent application Ser. Nos. 14/316,383; 14/316,398; 14/316,416; 14/316,431; 14/316,447; and 14/316,463, the full disclosures of which is hereby incorporated by reference in their entireties.

Briefly, in one exemplary process, beads are provided that each may include large numbers of the above described oligonucleotides releasably attached to the beads, where all of the oligonucleotides attached to a particular bead may include the same nucleic acid barcode sequence, but where a large number of diverse barcode sequences may be represented across the population of beads used. Typically, the population of beads may provide a diverse barcode sequence library that may include at least 1000 different barcode sequences, at least 10,000 different barcode sequences, at least 100,000 different barcode sequences, or in some cases, at least 1,000,000 different barcode sequences. Additionally, each bead may typically be provided with large numbers of oligonucleotide molecules attached. In particular, the number of molecules of oligonucleotides including the barcode sequence on an individual bead may be at least bout 10,000 oligonucleotides, at least 100,000 oligonucleotide molecules, at least 1,000,000 oligonucleotide molecules, at least 100,000,000 oligonucleotide molecules, and in some cases at least 1 billion oligonucleotide molecules.

The oligonucleotides may be releasable from the beads upon the application of a particular stimulus to the beads. In some cases, the stimulus may be a photo-stimulus, e.g., through cleavage of a photo-labile linkage that may release the oligonucleotides. In some cases, a thermal stimulus may be used, where elevation of the temperature of the beads environment may result in cleavage of a linkage or other release of the oligonucleotides form the beads. In some cases, a chemical stimulus may be used that cleaves a linkage of the oligonucleotides to the beads, or otherwise may result in release of the oligonucleotides from the beads.

In accordance with the methods and systems described herein, the beads including the attached oligonucleotides may be co-partitioned with the individual samples, such that a single bead and a single sample are contained within an individual partition. In some cases, where single bead partitions are desired, it may be desirable to control the relative flow rates of the fluids such that, on average, the partitions contain less than one bead per partition, in order to ensure that those partitions that are occupied, are primarily singly occupied. Likewise, one may wish to control the flow rate to provide that a higher percentage of partitions are occupied, e.g., allowing for only a small percentage of unoccupied partitions. In preferred aspects, the flows and channel architectures are controlled as to ensure a desired number of singly occupied partitions, less than a certain level of unoccupied partitions and less than a certain level of multiply occupied partitions.

Figure 3:
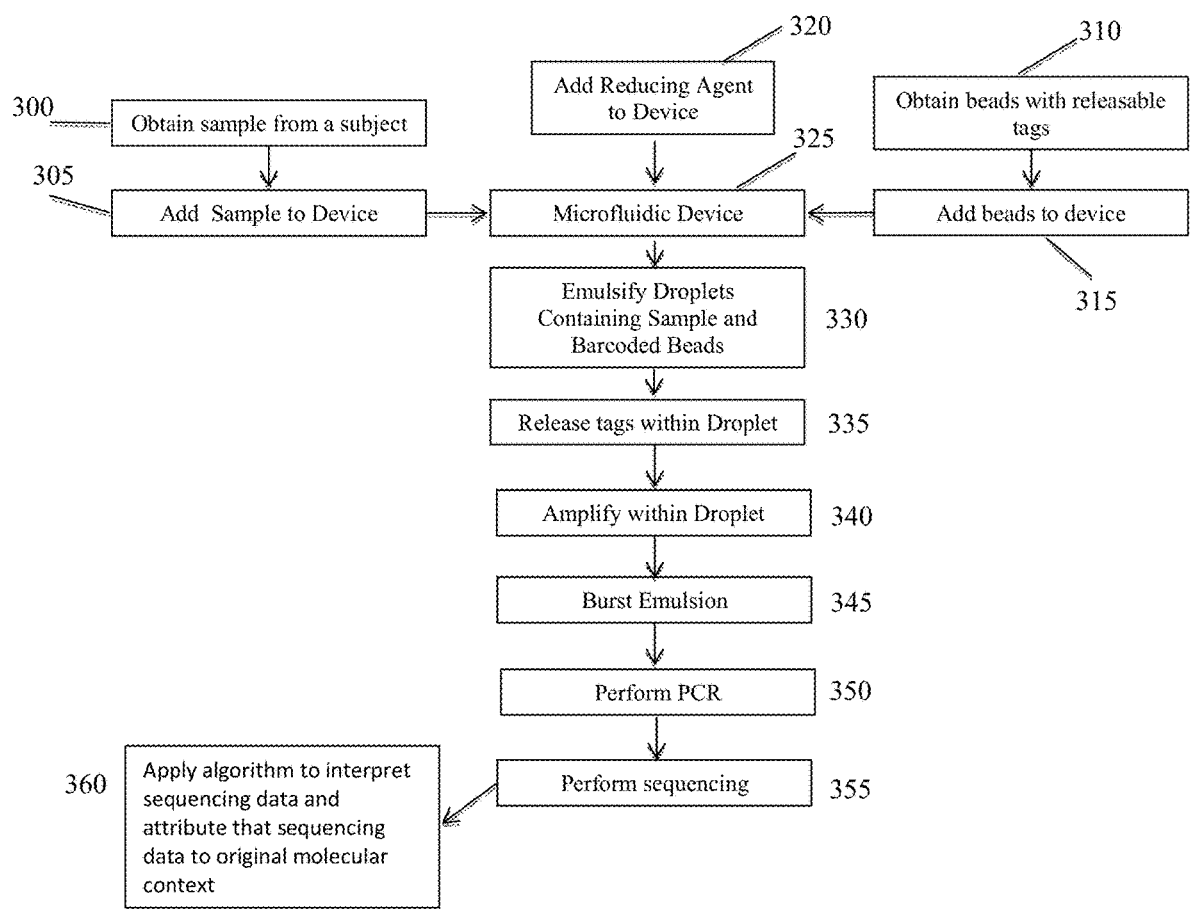
FIG. 3 illustrates a typical workflow for performing an assay to detect sequence information, using the methods and compositions disclosed herein.

FIG. 3 illustrates one particular example method for barcoding and subsequently sequencing a sample nucleic acid, particularly for use for a copy number variation or haplotype assay. First, a sample comprising nucleic acid may be obtained from a source, 300, and a set of barcoded beads may also be obtained, 310. The beads are preferably linked to oligonucleotides containing one or more barcode sequences, as well as a primer, such as a random N-mer or other primer. Preferably, the barcode sequences are releasable from the barcoded beads, e.g., through cleavage of a linkage between the barcode and the bead or through degradation of the underlying bead to release the barcode, or a combination of the two. For example, in certain preferred aspects, the barcoded beads can be degraded or dissolved by an agent, such as a reducing agent to release the barcode sequences. In this example, a low quantity of the sample comprising nucleic acid, 305, barcoded beads, 315, and optionally other reagents, e.g., a reducing agent, 320, are combined and subject to partitioning. By way of example, such partitioning may involve introducing the components to a droplet generation system, such as a microfluidic device, 325. With the aid of the microfluidic device 325, a water-in-oil emulsion 330 may be formed, wherein the emulsion contains aqueous droplets that contain sample nucleic acid, 305, reducing agent, 320, and barcoded beads, 315. The reducing agent may dissolve or degrade the barcoded beads, thereby releasing the oligonucleotides with the barcodes and random N-mers from the beads within the droplets, 335. The random N-mers may then prime different regions of the sample nucleic acid, resulting in amplified copies of the sample after amplification, wherein each copy is tagged with a barcode sequence, 340. Preferably, each droplet contains a set of oligonucleotides that contain identical barcode sequences and different random N-mer sequences. Subsequently, the emulsion is broken, 345 and additional sequences (e.g., sequences that aid in particular sequencing methods, additional barcodes, etc.) may be added, via, for example, amplification methods, 350 (e.g., PCR). Sequencing may then be performed, 355, and an algorithm applied to interpret the sequencing data, 360. Sequencing algorithms are generally capable, for example, of performing analysis of barcodes to align sequencing reads and/or identify the sample from which a particular sequence read belongs. In addition, and as is described herein, these algorithms may also further be used to attribute the sequences of the copies to their originating molecular context.

As will be appreciated, prior to or simultaneously with tagging with the barcode sequence 340, the samples can be amplified in accordance with any of the methods described herein to provide targeted coverage of selected regions of the genome. This targeted coverage generally results in a larger population of amplicons representing sequences of the nucleic acids (or portions of thereof) in a partition containing those selected regions of the genome as compared to amplicons from other regions of the genome. As a result, there will be a larger number of the amplified copies containing barcode sequence 340 within a partition from the selected regions of the genome than from other regions of the genome.

In some embodiments and in accordance with any of the above, different amplification protocols are used to favor amplification of fragments containing portions of selected regions of the genome than the protocols used to attach barcode sequences to the fragments. In one non-limiting example, the selective amplification using targeted PCR primers are conducted under standard PCR amplification thermal cycling conditions, whereas the amplification for attachment of the barcodes is conducted with a sharp drop in temperature followed by a slow ramp of increasing temperature to allow for the priming and extension of the random N-mers.

Figure 4:
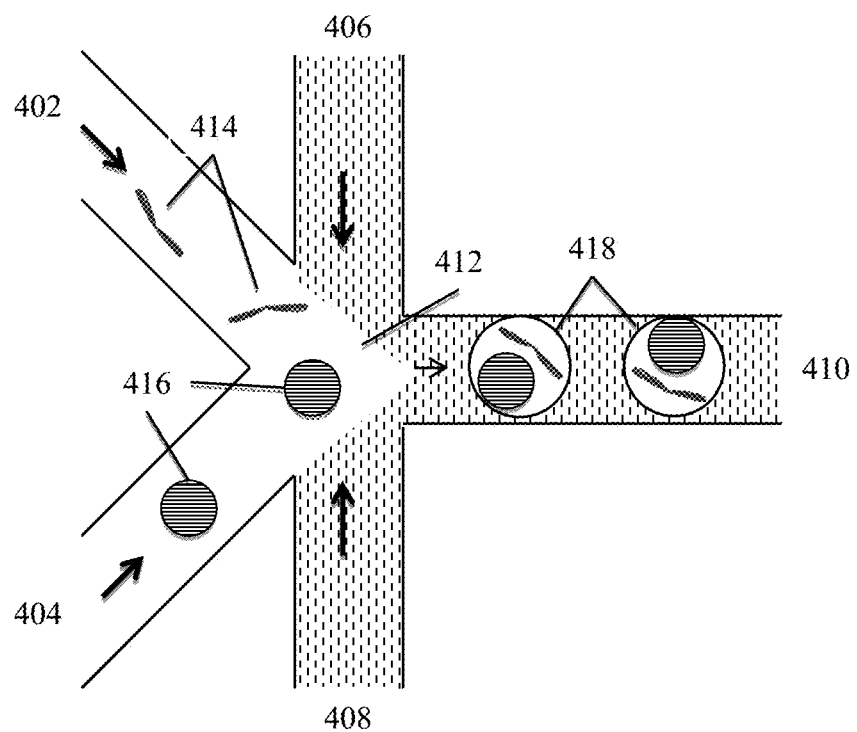
FIG. 4 provides a schematic illustration of a process for combining a nucleic acid sample with beads and partitioning the nucleic acids and beads into discrete droplets.

As noted above, while single occupancy may be the most desired state, it will be appreciated that multiply occupied partitions or unoccupied partitions may often be present. An example of a microfluidic channel structure for co-partitioning samples and beads comprising barcode oligonucleotides is schematically illustrated in FIG. 4. As shown, channel segments 402, 404, 406, 408 and 410 are provided in fluid communication at channel junction 412. An aqueous stream comprising the individual samples 414 is flowed through channel segment 402 toward channel junction 412. As described elsewhere herein, these samples may be suspended within an aqueous fluid prior to the partitioning process.

Concurrently, an aqueous stream comprising the barcode carrying beads 416 is flowed through channel segment 404 toward channel junction 412. A non-aqueous partitioning fluid is introduced into channel junction 412 from each of side channels 406 and 408, and the combined streams are flowed into outlet channel 410. Within channel junction 412, the two combined aqueous streams from channel segments 402 and 404 are combined, and partitioned into droplets 418, that include co-partitioned samples 414 and beads 416. As noted previously, by controlling the flow characteristics of each of the fluids combining at channel junction 412, as well as controlling the geometry of the channel junction, one can optimize the combination and partitioning to achieve a desired occupancy level of beads, samples or both, within the partitions 418 that are generated.

As will be appreciated, a number of other reagents may be co-partitioned along with the samples and beads, including, for example, chemical stimuli, nucleic acid extension, transcription, and/or amplification reagents such as polymerases, reverse transcriptases, nucleoside triphosphates or NTP analogues, primer sequences and additional cofactors such as divalent metal ions used in such reactions, ligation reaction reagents, such as ligase enzymes and ligation sequences, dyes, labels, or other tagging reagents. The primer sequences may include random primer sequences or targeted PCR primers directed to amplifying selected regions of the genome or a combination thereof.

Once co-partitioned, the oligonucleotides disposed upon the bead may be used to barcode and amplify the partitioned samples. A particularly elegant process for use of these barcode oligonucleotides in amplifying and barcoding samples is described in detail in U.S. patent application Ser. Nos. 14/316,383; 14/316,398; 14/316,416; 14/316,431; 14/316,447; and 14/316,463, the full disclosures of which are hereby incorporated by reference in their entireties. Briefly, in one aspect, the oligonucleotides present on the beads that are co-partitioned with the samples and released from their beads into the partition with the samples. The oligonucleotides typically include, along with the barcode sequence, a primer sequence at its 5' end. The primer sequence may be random or structured. Random primer sequences are generally intended to randomly prime numerous different regions of the samples. Structured primer sequences can include a range of different structures including defined sequences targeted to prime upstream of a specific targeted region of the sample as well as primers that have some sort of partially defined structure, including without limitation primers containing a percentage of specific bases (such as a percentage of GC N-mers), primers containing partially or wholly degenerate sequences, and/or primers containing sequences that are partially random and partially structured in accordance with any of the description herein. As will be appreciated, any one or more of the above types of random and structured primers may be included in oligonucleotides in any combination.

Figure 5:
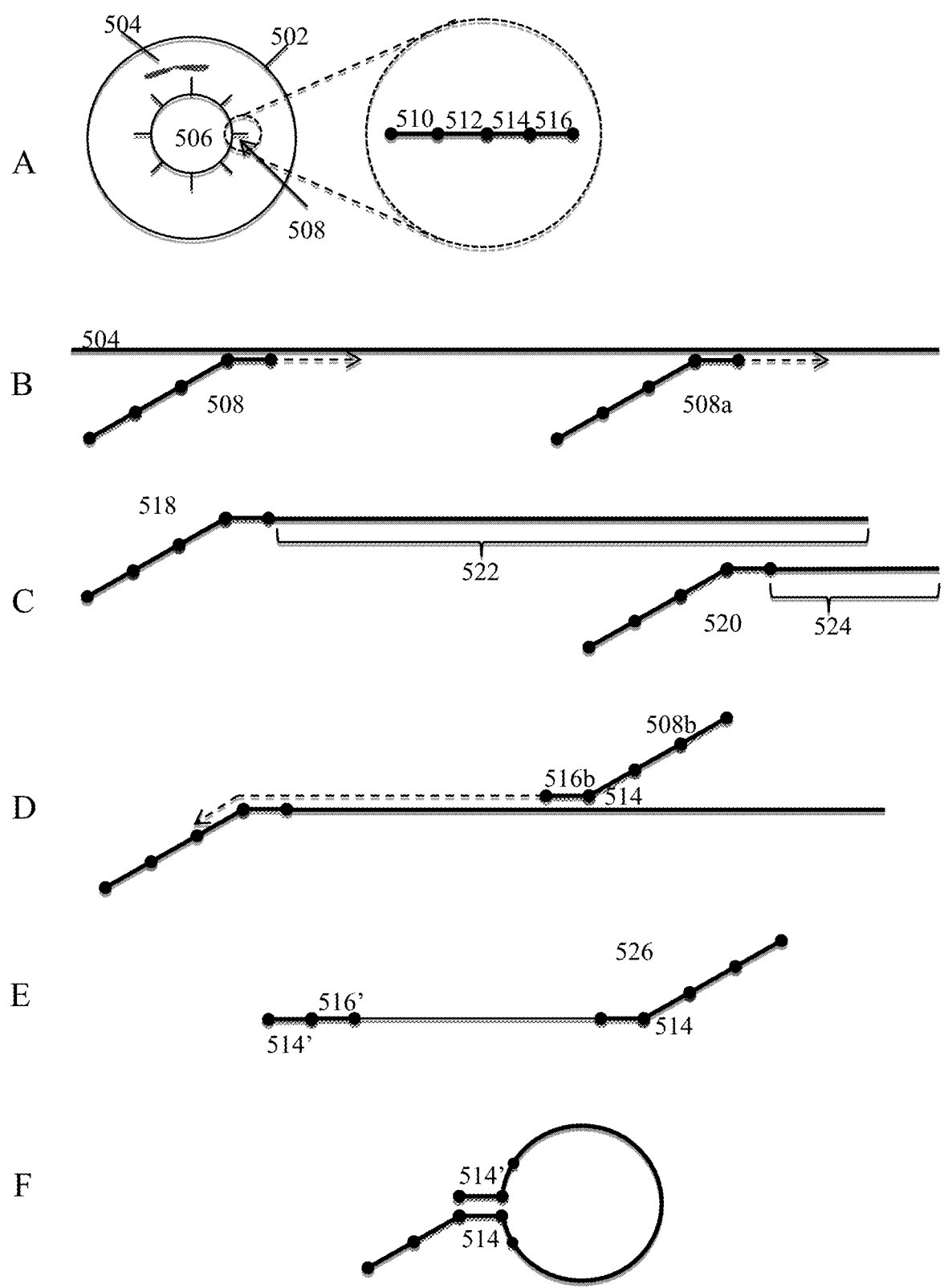
FIG. 5 provides a schematic illustration of a process for barcoding and amplification of chromosomal nucleic acid fragments.

Once released, the primer portion of the oligonucleotide can anneal to a complementary region of the sample. Extension reaction reagents, e.g., DNA polymerase, nucleoside triphosphates, co-factors (e.g., Mg2+ or Mn2+ etc.), that are also co-partitioned with the samples and beads, then extend the primer sequence using the sample as a template, to produce a complementary fragment to the strand of the template to which the primer annealed, with complementary fragment includes the oligonucleotide and its associated barcode sequence. Annealing and extension of multiple primers to different portions of the sample may result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In some cases, this replication process is configured such that when the first complement is duplicated, it produces two complementary sequences at or near its termini, to allow the formation of a hairpin structure or partial hairpin structure, which reduces the ability of the molecule to be the basis for producing further iterative copies. A schematic illustration of one example of this is shown in FIG. 5.

As the figure shows, oligonucleotides that include a barcode sequence are co-partitioned in, e.g., a droplet 502 in an emulsion, along with a sample nucleic acid 504. As noted elsewhere herein, the oligonucleotides 508 may be provided on a bead 506 that is co-partitioned with the sample nucleic acid 504, which oligonucleotides are preferably releasable from the bead 506, as shown in panel A. The oligonucleotides 508 include a barcode sequence 512, in addition to one or more functional sequences, e.g., sequences 510, 514 and 516. For example, oligonucleotide 508 is shown as comprising barcode sequence 512, as well as sequence 510 that may function as an attachment or immobilization sequence for a given sequencing system, e.g., a P5 sequence used for attachment in flow cells of an Illumina Hiseq or Miseq system. As shown, the oligonucleotides also include a primer sequence 516, which may include a random or targeted N-mer for priming replication of portions of the sample nucleic acid 504. Also included within oligonucleotide 508 is a sequence 514 which may provide a sequencing priming region, such as a "read1" or R1 priming region, that is used to prime polymerase mediated, template directed sequencing by synthesis reactions in sequencing systems. In many cases, the barcode sequence 512, immobilization sequence 510 and R1 sequence 514 may be common to all of the oligonucleotides attached to a given bead. The primer sequence 516 may vary for random N-mer primers, or may be common to the oligonucleotides on a given bead for certain targeted applications.

Based upon the presence of primer sequence 516, the oligonucleotides are able to prime the sample nucleic acid as shown in panel B, which allows for extension of the oligonucleotides 508 and 508a using polymerase enzymes and other extension reagents also co-portioned with the bead 506 and sample nucleic acid 504. As shown in panel C, following extension of the oligonucleotides that, for random N-mer primers, would anneal to multiple different regions of the sample nucleic acid 504; multiple overlapping complements or fragments of the nucleic acid are created, e.g., fragments 518 and 520. Although including sequence portions that are complementary to portions of sample nucleic acid, e.g., sequences 522 and 524, these constructs are generally referred to herein as comprising fragments of the sample nucleic acid 504, having the attached barcode sequences. As will be appreciated, the replicated portions of the template sequences as described above are often referred to herein as "fragments" of that template sequence. Notwithstanding the foregoing, however, the term "fragment" encompasses any representation of a portion of the originating nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In preferred aspects, however, fragments of a template or sample nucleic acid sequence will denote replicated portions of the underlying sequence or complements thereof.

The barcoded nucleic acid fragments may then be subjected to characterization, e.g., through sequence analysis, or they may be further amplified in the process, as shown in panel D. For example, additional oligonucleotides, e.g., oligonucleotide 508b, also released from bead 506, may prime the fragments 518 and 520. In particular, again, based upon the presence of the random N-mer primer 516b in oligonucleotide 508b (which in many cases will be different from other random N-mers in a given partition, e.g., primer sequence 516), the oligonucleotide anneals with the fragment 518, and is extended to create a complement 526 to at least a portion of fragment 518 which includes sequence 528, that comprises a duplicate of a portion of the sample nucleic acid sequence. Extension of the oligonucleotide 508b continues until it has replicated through the oligonucleotide portion 508 of fragment 518. As noted elsewhere herein, and as illustrated in panel D, the oligonucleotides may be configured to prompt a stop in the replication by the polymerase at a desired point, e.g., after replicating through sequences 516 and 514 of oligonucleotide 508 that is included within fragment 518. As described herein, this may be accomplished by different methods, including, for example, the incorporation of different nucleotides and/or nucleotide analogues that are not capable of being processed by the polymerase enzyme used. For example, this may include the inclusion of uracil containing nucleotides within the sequence region 512 to prevent a non-uracil tolerant polymerase to cease replication of that region. As a result a fragment 526 is created that includes the full-length oligonucleotide 508b at one end, including the barcode sequence 512, the attachment sequence 510, the R1 primer region 514, and the random N-mer sequence 516b. At the other end of the sequence will be included the complement 516' to the random N-mer of the first oligonucleotide 508, as well as a complement to all or a portion of the R1 sequence, shown as sequence 514'. The R1 sequence 514 and its complement 514' are then able to hybridize together to form a partial hairpin structure 528. As will be appreciated because the random N-mers differ among different oligonucleotides, these sequences and their complements would not be expected to participate in hairpin formation, e.g., sequence 516', which is the complement to random N-mer 516, would not be expected to be complementary to random N-mer sequence 516b. This would not be the case for other applications, e.g., targeted primers, where the N-mers would be common among oligonucleotides within a given partition. By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 526.

Figure 6A:
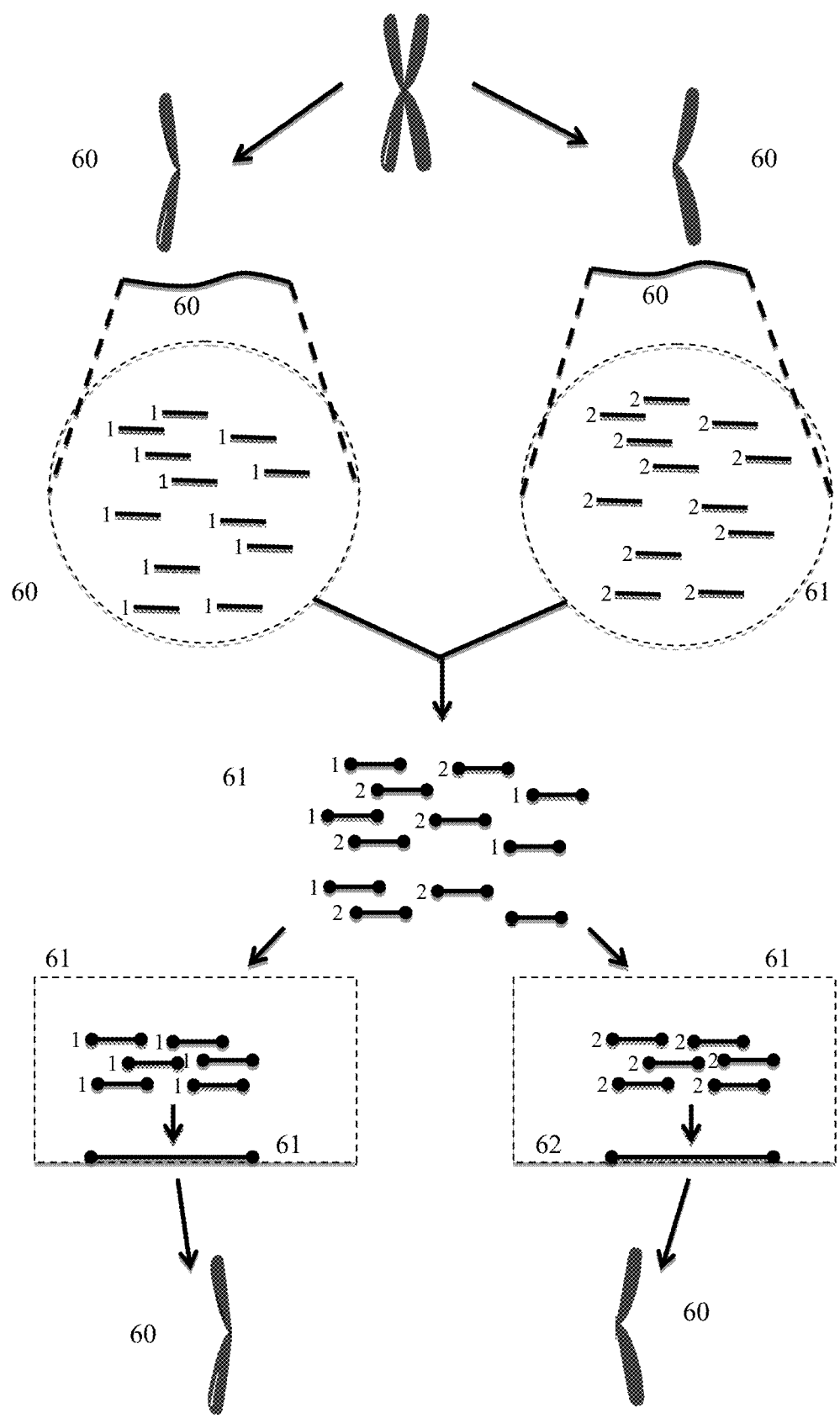
FIGS. 6A and B provide schematic illustrations of the use of barcoding of nucleic acid fragments in attributing sequence data to their originating source nucleic acid molecule.

All of the fragments from multiple different partitions may then be pooled for sequencing on high throughput sequencers as described herein. Because each fragment is coded as to its partition of origin, the sequence of that fragment may be attributed back to its origin based upon the presence of the barcode. This is schematically illustrated in FIG. 6A. As shown in one example, a nucleic acid 604 originated from a first source 600 (e.g., individual chromosome, strand of nucleic acid, etc.) and a nucleic acid 606 derived from a different chromosome 602 or strand of nucleic acid are each partitioned along with their own sets of barcode oligonucleotides as described above.

Within each partition, each nucleic acid 604 and 606 is then processed to separately provide overlapping set of second fragments of the first fragment(s), e.g., second fragment sets 608 and 610. This processing also provides the second fragments with a barcode sequence that is the same for each of the second fragments derived from a particular first fragment. As shown, the barcode sequence for second fragment set 608 is denoted by "1" while the barcode sequence for fragment set 610 is denoted by "2". A diverse library of barcodes may be used to differentially barcode large numbers of different fragment sets. However, it is not necessary for every second fragment set from a different first fragment to be barcoded with different barcode sequences. In fact, in many cases, multiple different first fragments may be processed concurrently to include the same barcode sequence. Diverse barcode libraries are described in detail elsewhere herein.

The barcoded fragments, e.g., from fragment sets 608 and 610, may then be pooled for sequencing using, for example, sequence by synthesis technologies available from Illumina or Ion Torrent division of Thermo Fisher, Inc. Once sequenced, the sequence reads from the pooled fragments 612 can be attributed to their respective fragment set, e.g., as shown in aggregated reads 614 and 616, at least in part based upon the included barcodes, and optionally, and preferably, in part based upon the sequence of the fragment itself. The attributed sequence reads for each fragment set are then assembled to provide the assembled sequence for each sample fragment, e.g., sequences 618 and 620, which in turn, may be further attributed back to their respective original chromosomes or source nucleic acid molecules (600 and 602). Methods and systems for assembling genomic sequences are described in, for example, U.S. patent application Ser. No. 14/752,773, filed Jun. 26, 2015, the full disclosure of which is hereby incorporated by reference in its entirety.

Figure 6B:
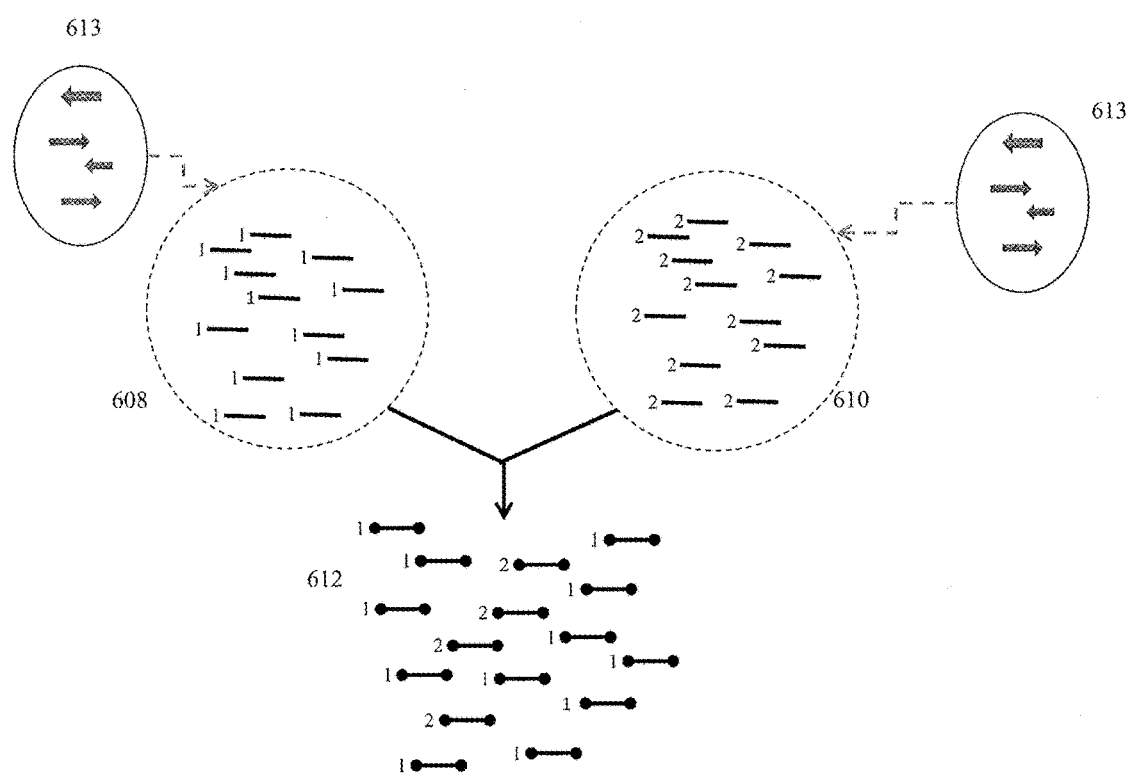

In some embodiments and as illustrated in FIG. 6B, included with the partitions containing fragment sets 608 or 610 are primer sets 613. The primer sets 613 are in further embodiments directed to selected regions of the genome, such that prior to, simultaneously with or subsequent to providing the barcode sequences (barcode "1" for 608 and "2" for 610), the fragment sets 608 and 610 are amplified such that the selected regions of the genome are covered to an additional extent over other regions of the genome. In the exemplary embodiment pictured in FIG. 6B, fragment set 608 contain sequences from the selected regions of the genome to which primer sets 613 are directed, but fragment set 610 does not contain sequences from those selected regions of the genome. As such, there will be increased coverage (e.g., more copies) of fragments from set 608 than from set 610. Thus, the pooled fragments 612 contains barcoded fragments contain fragments that have been amplified in a targeted way, allowing for a larger proportion of sequence reads from fragment set 608 (the "1" barcoded fragments) than from fragment set 610 (the "2" barcoded fragments). In addition, due to the barcodes, that larger proportion of sequence reads from set 608 can, like the remainder of the fragments in pooled set 612, be attributed back to their respective original source nucleic acid molecules 600 and 602 (shown in FIG. 6A).

III. Application of Methods and Systems to Nucleic Acid Sequencing

The methods, compositions, and systems described herein are particularly amenable for use in nucleic acid sequencing technologies. Such sequencing technologies can include any technologies known in the art, including short-read and long-read sequencing technologies. In certain aspects, the methods, compositions and systems described herein are used in short read, high accuracy sequencing technologies.

The methods, compositions, and systems described herein allow for genetic characterization of regions of the genome that are poorly characterized, are highly polymorphic, and/or diverge from reference sequences. In particular, the methods, compositions and systems described herein provide increased and redundant coverage of selected portions of the genome such that additional redundant sequence information can be obtained from those selected portion of the genome. In specific instances, that additional sequence information (e.g., increased coverage of targeted regions of the genome) provides enough information to allow for de novo sequencing of those selected portions of the genome. This de novo sequencing is of particular use for regions of the genome that are poorly characterized, are highly polymorphic, and/or diverge from reference sequences. As will be appreciated, a significant percentage (at least 5-10% according to, for example Altemose et al., PLOS Computational Biology, May 15, 2014, Vol. 10, Issue 5) of the human genome remains unassembled, unmapped, and poorly characterized. The reference assembly generally annotates these missing regions as multi-megabase heterochromatic gaps, found primarily near centromeres and on the short arms of the acrocentric chromosomes. This missing fraction of the genome includes structural features that remain resistant to accurate characterization using generally used sequencing technologies. Additional exemplary regions that are resistant to accurate characterization include without limitation areas that have close homologous pseudogenes (for example SMN1/2 Cyp2d6), areas that have substantial repeated sequences throughout the genome, including without limitation transposons (such as SINEs, LINEs), as well as areas that have tremendous variation for which reference sequences serve as a poor guide (such as the regions encoding the genes for the human leukocyte antigen (HLA) complex). The methods, compositions, and systems described herein combine selective amplification of the regions of interest with the ability to maintain molecular context, thereby allowing for de novo sequencing of genomic regions that are generally poorly characterized.

In specific instances, methods described herein include a step in which selected regions of the genome are selectively amplified prior to sequencing. This amplification, which is generally conducted using methods known in the art (including without limitation PCR amplification) provides at least 1×, 2×, 3×, 4×, 5×, 6×, 7×, 8×, 9×, 10×, 11×, 12×, 13×, 14×, 15×, 16×, 17×, 18×, 19×, or 20× coverage of the selected regions of the genome, thereby providing a quantity of nucleic acids to allow de novo sequencing of those selected regions. In further embodiments, the amplification provides at least 1×-30×, 2×-25×, 3×-20×, 4×-15×, or 5×-10× coverage of the selected regions of the genome.

The amplification is generally conducted through extension of primers complementary to sequences within or near the selected regions of the genome. In some cases, a library of primers is used that is designed to tile across the regions of interest—in other words, the library of primer is designed to amplify regions at specific distances along the selected regions of the genome. In some instances, the selective amplification utilizes primers that are complementary to every 10, 15, 20, 25, 50, 100, 200, 250, 500, 750, 1000, or 10000 bases along the selected regions of the genome. In still further examples, the tiled library of primers is designed to capture a mixture of distances—that mixture can be a random mixture of distances or intelligently designed such that specific portions or percentages of the selected regions are amplified by different primer pairs. In further embodiments, the primer pairs are designed such that each pair amplifies about 1-5%, 2-10%, 3-15%, 4-20%, 5-25%, 6-30%, 7-35%, 8-40%, 9-45%, or 10-50% of any contiguous region of a selected portion of the genome.

In certain embodiments and in accordance with any of the description above, the amplification occurs across a region of the genome that is at least 3 megabasepairs long (Mb). In further embodiments, the selected region of the genome that is selectively amplified in accordance with any of the methods described herein is at least 3.5, 4, 4.5, 5, 5.5, 6, 6.5, 7, 7.5, 8, 8.5, 9, 9.5, or 10 Mb. In yet further embodiments, the selected region of the genome is about 2-20, 3-18, 4-16, 5-14, 6-12, or 7-10 Mb in length. As discussed above, amplification may occur across these regions using a single primer pair complementary to sequences at the ends or near the ends of these regions. In other embodiments, amplification is conducted with a library of primer pairs that are tiled across the length of the region, such that regular segments, random segments, or some combination of different segment distances along the region are amplified, with the extent of coverage in accordance with the description above.

In some embodiments, the primers used in selective amplification of selected regions of the genome contain uracils so that the primers themselves are not amplified.

In general, the methods and systems described herein accomplish targeted genomic sequencing by providing for the determination of the sequence of selected regions of the genome, and this sequencing information is generally obtained using methods that have the advantages of the extremely low sequencing error rates and high throughput of short read sequencing technologies. As described previously, an advantage of the methods and systems described herein is that they can achieve the desired results through the use of ubiquitously available, short read sequencing technologies. Such technologies have the advantages of being readily available and widely dispersed within the research community, with protocols and reagent systems that are well characterized and highly effective. These short read sequencing technologies include those available from, e.g., Illumina, inc. (GAIIx, NextSeq, MiSeq, HiSeq, ×10), Ion Torrent division of Thermo-Fisher (Ion Proton and Ion PGM), pyrosequencing methods, as well as others.

Of particular advantage is that the methods and systems described herein utilize these short read sequencing technologies and do so with their associated low error rates. In particular, the methods and systems described herein achieve the desired individual molecular readlengths or context, as described above, but with individual sequencing reads, excluding mate pair extensions, that are shorter than 1000 bp, shorter than 500 bp, shorter than 300 bp, shorter than 200 bp, shorter than 150 by or even shorter; and with sequencing error rates for such individual molecular readlengths that are less than 5%, less than 1%, less than 0.5%, less than 0.1%, less than 0.05%, less than 0.01%, less than 0.005%, or even less than 0.001%.

Methods of processing and sequencing nucleic acids in accordance with the methods and systems described in the present application are also described in further detail in U.S. Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material.

Figure 7:
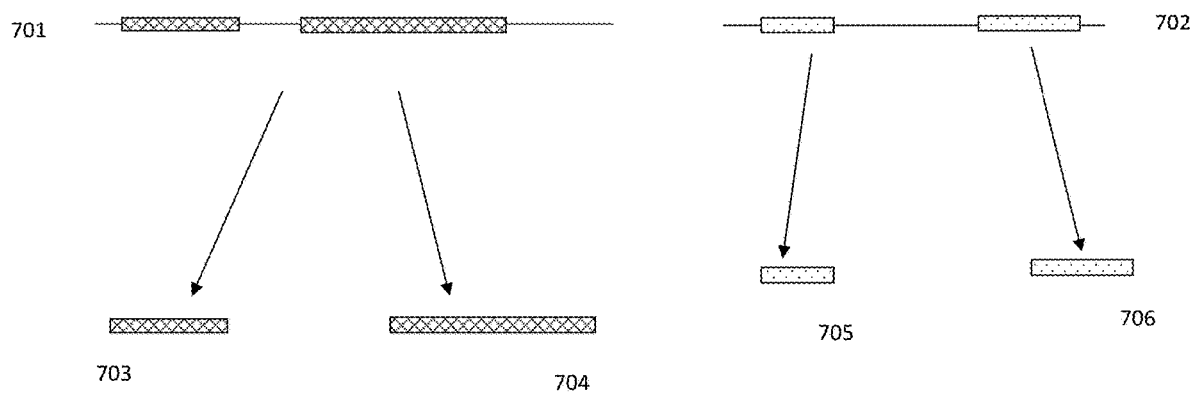
FIG. 7 provides a schematic illustration of an embodiment of the invention.

Regardless of the sequencing platform used, in general and in accordance with any of the methods described herein, sequencing of nucleic acids is typically carried out in a manner that preserves the molecular context of sequence reads or portions of sequence reads. By that is meant that multiple sequence reads or multiple portions of sequence reads may be attributable to a single originating molecule of a nucleic acid. By 'attributable to' is meant that the sequence reads can be identified as falling within the linear sequence of bases of their particular originating molecules of a nucleic acid—in other words, and in reference to FIG. 7, if fragments 703, 704, 705 and 706 are generated from originating nucleic acid molecules 701 and 702, then the sequencing is carried out in a manner such that sequence reads from fragments 703, 704, 705 and 706 retain their molecular context and it is readily ascertained that fragments 703 and 704 are derived from originating molecule 701 whereas 705 and 706 are derived from originating molecule 702, even if all the fragments are pooled together for the sequencing reaction. In addition, the sequencing is generally conducted such that not only is the originating molecule ascertained, but so also is the relative position of each fragment along that linear molecule—e.g., it can be determined that fragment 703 is "upstream" from fragment 704 along the linear sequence of originating nucleic acid 701. In general, molecular context is retained through the use of any identifier or any other method of distinguishing one or more fragments from other fragments. In general, such identifiers are used on fragments that have been separated into groups or into individual entities. In some examples, such separation is separation into discrete partitions, although, as will be appreciated, any other methods of separating molecules can be used. In still further examples, the identifiers used are barcodes, and the linear position is determined both through barcoding as well as algorithmic assembly of sequence reads from overlapping fragments. Although for the sake of clarity much of the discussion herein is in terms of separation into partitions and/or barcoding, it will be appreciated that any methods of separating originating nucleic acid molecules and any methods of identifying or otherwise attributing fragments are of use in the methods and systems described herein.

As will be appreciated, while the single originating molecule of a nucleic acid may be of any of a variety of lengths, in preferred aspects, it will be a relatively long molecule, allowing for preservation of long range molecular context. In particular, the single originating molecule is preferably substantially longer than the typical short read sequence length, e.g., longer than 200 bases, and is often at least 1000 bases or longer, 5000 bases or longer, 10,000 bases or longer, 20,000 bases or longer, 30,000 bases or longer, 40,000 bases or longer, 50,000 bases or longer, 60,000 bases or longer, 70,000 bases or longer, 80,000 bases or longer, 90,000 bases or longer, or 100,000 bases or longer, and in some cases 1 megabase or longer.

In certain situations, sequencing methods described herein include a combination of deep coverage of the selected regions with lower level linked reads across longer ranges of the genome. As will be appreciated, this combination of de novo and re-sequencing provides an efficient way to sequence an entire genome and/or large portions of a genome. Targeted coverage of poorly characterized and/or highly polymorphic regions through the selective amplification methods described herein provides the amount of nucleic acid material necessary for de novo sequence assembly, whereas linked genomic sequencing over other regions of the genome maintains high throughput sequencing of the remainder of the genome. The methods and compositions described herein are uniquely amenable to allowing for this combination of de novo and linked read sequencing, because the same sequencing platform can be used for both types of coverage. The population of nucleic acids and/or nucleic acid fragments that are sequenced in accordance with the methods described herein contain sequences from both the genomic regions for de novo sequencing and the genomic regions for re-sequencing—the proportion of nucleic acids covering the regions of interest for de novo sequencing is higher than the nucleic acids covering the other regions of the genome due to the targeted amplification methods described in further detail herein.

In general, as shown in FIG. 1, the methods and systems described herein may be used to characterize nucleic acids, particularly nucleic acids from selected regions of the genome, while retaining molecular context. As shown, two discrete individual nucleic acids 102 and 104 are illustrated, each having a number of regions of interest, e.g., region 106 and 108 in nucleic acid 102, and regions 110 and 112 in nucleic acid 104. The regions of interest in each nucleic acid are linked within (e.g., originate from) the same nucleic acid molecule, but in some cases these regions may be relatively separated from each other, e.g., more than 1 kb apart, more than 5 kb apart, more than 10 kb apart, more than 20 kb apart, more than 30 kb apart, more than 40 kb apart, more than 50 kb apart, and in some cases, as much as 100 kb apart. The regions of interest are generally discrete and separate parts of the genome—in some cases, such regions are poorly characterized regions. The regions of interest may also denote individual genes, gene groups, exons. As shown, each nucleic acid 102 and 104 is separated into its own partition 114 and 116, respectively. As noted elsewhere herein, these partitions are, in many cases, aqueous droplets in a water in oil emulsion. Within each droplet, portions of each fragment are copied in a manner that preserves the original molecular context of those fragments, e.g., as having originated from the same molecule. As shown, this is achieved through the inclusion in each copied fragment of a barcode sequence, e.g., barcode sequence "1" or "2" as illustrated, that is representative of the droplet into which the originating fragment was partitioned. For whole genome sequence analysis applications, one could simply pool all of the copied fragments and their associated barcodes, in order to sequence and reassemble the full range sequence information from each of the originating nucleic acids 102 and 104. However, in many cases, it is more desirable to only analyze specific targeted portions of the overall genome, in order to provide greater focus on scientifically relevant portions of the genome, and to minimize the time and expense of performing sequencing on less relevant or irrelevant portions of the genome.

In accordance with the above, in addition to the barcoding step, there may be one or more steps of selective amplification, such that if nucleic acids 102 or 104 contain selected genomic regions of interest, amplicons from those regions will form a larger percentage of the fragments in each of the partitions 114 and 116. This amplification step will generally take place prior to or simultaneously with the attachment of the barcodes in accordance with the methods described herein, although in some embodiments the amplification step may also occur subsequent to attachment of the barcodes.

Because the pooled fragments within library 118 retain their original molecular context, e.g., through the retention of the barcode information, they may be reassembled into their original molecular contexts with embedded (at times, long range) linkage information, e.g., with inferred linkage as between each of the assembled regions of interest 106:108 and 110:112. By way of example, one may identify direct molecular linkage between two disparate targeted portions of the genome, e.g., two or more exons, and that direct molecular linkage may be used to identify structural variations and other genomic characteristics. For situations in which selective amplification is utilized to increase the amount of nucleic acid fragments containing portions of selected regions of the genome, then the ability to identify the molecular context also provides a way to sequence those selected regions of the genome, often at a depth that allows for de novo assembly of those regions.

Generally, methods of the invention include steps as illustrated in FIG. 2, which provides a schematic overview of methods of the invention discussed in further detail herein. As will be appreciated, the method outlined in FIG. 2 is an exemplary embodiment that may be altered or modified as needed and as described herein.

As shown in FIG. 2, the methods described herein will in most examples include a step in which sample nucleic acids containing the targeted regions of interest are partitioned (201). Generally, each partition containing nucleic acids from genomic regions of interest will undergo a targeted enrichment to produce a population of fragments in which a large proportion will contain sequences from a selected genomic region (202). Those fragments are then further fragmented or copied in such a way as to preserve the original molecular context of the fragments (203), usually by barcoding the fragments that are specific to the partition in which they are contained. Each partition may in some examples include more than one nucleic acid, and will in some instances contain several hundred nucleic acid molecules—in situations in which multiple nucleic acids are within a partition, any particular locus of the genome will generally be represented by a single individual nucleic acid prior to barcoding. The barcoded fragments of step 203 can be generated using any methods known in the art—in some examples, oligonucleotides are the samples within the distinct partitions. Such oligonucleotides may comprise random sequences intended to randomly prime numerous different regions of the samples, or they may comprise a specific primer sequence targeted to prime upstream of a targeted region of the sample. In further examples, these oligonucleotides also contain a barcode sequence, such that the replication process also barcodes the resultant replicated fragment of the original sample nucleic acid. A particularly elegant process for use of these barcode oligonucleotides in amplifying and barcoding samples is described in detail in U.S. patent application Ser. Nos. 14/316,383; 14/316,398; 14/316,416; 14/316,431; 14/316,447; and 14/316,463 which are herein incorporated by reference in their entirety for all purposes and in particular for all written description, figures and working examples directed to processing nucleic acids and sequencing and other characterizations of genomic material. Extension reaction reagents, e.g., DNA polymerase, nucleoside triphosphates, co-factors (e.g., $Mg^{2+}$ or $Mn^{2+}$ etc.), that are also contained in the partitions, then extend the primer sequence using the sample as a template, to produce a complementary fragment to the strand of the template to which the primer annealed, and the complementary fragment includes the oligonucleotide and its associated barcode sequence. Annealing and extension of multiple primers to different portions of the sample can result in a large pool of overlapping complementary fragments of the sample, each possessing its own barcode sequence indicative of the partition in which it was created. In some cases, these complementary fragments may themselves be used as a template primed by the oligonucleotides present in the partition to produce a complement of the complement that again, includes the barcode sequence. In further examples, this replication process is configured such that when the first complement is duplicated, it produces two complementary sequences at or near its termini to allow the formation of a hairpin structure or partial hairpin structure, which reduces the ability of the molecule to be the basis for producing further iterative copies.

Returning to the method exemplified in FIG. 2, once the partition-specific barcodes are attached to the copied fragments, the barcoded fragments are then pooled (204). The pooled fragments are then sequenced (205) and the sequences of the fragments are attributed to their originating molecular context (206), such that the targeted regions of interest are both identified and also linked with that originating molecular context. An advantage of the methods and systems described herein is that attaching a partition- or sample-specific barcode to the copied fragments prior to enriching the fragments for targeted genomic regions preserves the original molecular context of those targeted regions, allowing them to be attributed to their original partition and thus their originating sample nucleic acid.

In addition to the above workflow, targeted genomic regions may be further enriched, isolated or separated, i.e., "pulled down," for further analysis, particularly sequencing, using methods that include both chip-based and solution-based capture methods. Such methods utilize probes that are complementary to the genomic regions of interest or to regions near or adjacent to the genomic regions of interest. For example, in hybrid (or chip-based) capture, microarrays containing capture probes (usually single-stranded oligonucleotides) with sequences that taken together cover the region of interest are fixed to a surface. Genomic DNA is fragmented and may further undergo processing such as end-repair to produce blunt ends and/or addition of additional features such as universal priming sequences. These fragments are hybridized to the probes on the microarray. Unhybridized fragments are washed away and the desired fragments are eluted or otherwise processed on the surface for sequencing or other analysis, and thus the population of fragments remaining on the surface is enriched for fragments containing the targeted regions of interest (e.g., the regions comprising the sequences complementary to those contained in the capture probes). The enriched population of fragments may further be amplified using any amplification technologies known in the art. Exemplary methods for such targeted pull down enrichment methods are described in U.S. Ser. No. 14/927,297, filed on Oct. 29, 2015, which is hereby incorporated by reference in its entirety for all purposes and in particular for all teachings related to targeted pull down enrichment methods and sequencing methods, including all written description, figures and examples.

In some aspects, methods for coverage of selected regions of the genome include methods in which the discrete partitions containing nucleic acid molecules and/or fragments thereof from those selected regions are themselves sorted for further processing. As will be appreciated, this sorting of the discrete partitions may take place in any combination with other methods of selective amplification and/or targeted pull-down of genomic regions of interest described herein, in particular in any combination with the steps of the work flow described above.

In general, such methods of sorting of the discrete partitions includes steps in which partitions containing at least a portion of the one or more selected portions of the genome are separated from partitions that do not contain any sequences from those portions of the genome. These methods include the steps of providing a population enriched for sequences of the fragments comprising at least a portion of the one or more selected portions of the genome within the discrete partitions containing sequences from those portions of the genome. Such enrichment is generally accomplished through the use of directed PCR amplification of the fragments within the discrete partitions that include at least a portion of the one or more selected portions of the genome to produce a population. This directed PCR amplification thus produces amplicons comprising at least a portion of the one or more selected portions of the genome. In certain embodiments, these amplicons are attached to a detectable label, which in some non-limiting embodiments may include a fluorescent molecule. In general, such attachment occurs such that only those amplicons generated from the fragments containing the one or more selected portions of the genome are attached to the detectable label. In some embodiments, the attachment of the detectable labels occurs during the selective amplification of the one or more selected portions of the genome. Such detectable labels may in further embodiments include without limitation fluorescent labels, electrochemical labels, magnetic beads, and nanoparticles. This attachment of the detectable label can be accomplished using methods known in the art. In yet further embodiments, discrete partitions containing fragments comprising at least a portion of the one or more selected portions of the genome are sorted based on signals emitted from the detectable labels attached to the amplicons within those partitions.

In further embodiments, the steps of sorting discrete partitions containing selected portions of the genome from those that do not contain such sequences include the steps of (a) providing starting genomic material; (b) distributing individual nucleic acid molecules from the starting genomic material into discrete partitions such that each discrete partition contains a first individual nucleic acid molecule; (c) providing a population within at least some of the discrete partitions that is enriched for sequences of the fragments comprising at least a portion of the one or more selected portions of the genome; (d) attaching a common barcode sequence to the fragments within each discrete partition such that each of the fragments is attributable to the discrete partition in which it was contained; (e) separating discrete partitions containing fragments comprising at least a portion of the one or more selected portions of the genome from discrete partitions containing no fragments comprising the one or more selected portions of the genome; (f) obtaining sequence information from the fragments comprising at least a portion of the one or more selected portions of the genome, thereby sequencing one or more targeted portions of the genomic sample while retaining molecular context.

In further embodiments and in accordance with any of the above, prior to obtaining sequence information from the fragments, the discrete partitions are combined and the fragments are pooled together. In further embodiments, the step of obtaining sequence information from the fragments is conducted in such a way as to maintain the molecular context of the sequences of the fragments, such that the identifying further comprises identifying fragments derived from the same first individual nucleic acid molecules. In still further embodiments, this obtaining of sequence information includes a sequencing reaction selected from the group consisting of: short read-length sequencing reactions and long read-length sequencing reactions. In yet further embodiments, the sequencing reaction is a short read, high accuracy sequencing reaction.

In still further embodiments and in accordance with any of the above, the discrete partitions comprise droplets in an emulsion. In further embodiments, the barcoded fragments within the discrete partitions represent about 1×-10× coverage of the one or more selected portions of the genome. In still further embodiments, the barcoded fragments within the discrete partitions represent about 2×-5× coverage of the one or more selected portions of the genome. In yet further embodiments, the barcoded fragments of the amplicons within the discrete partitions represent at least 1× coverage of the one or more selected portions of the genome. In still further embodiments, the barcoded fragments within the discrete partitions represent at least 2× or 5× coverage of the one or more selected portions of the genome.

In addition to providing the ability to obtain sequence information from selected regions of the genome, the methods and systems described herein can also provide other characterizations of genomic material, including without limitation haplotype phasing, identification of structural variations, and identifying copy number variations, as described in U.S. patent application Ser. Nos. 14/752,589 and 14/752,602, which are herein incorporated by reference in their entirety for all purposes and in particular for all written description, figures and working examples directed to characterization of genomic material.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. As will be appreciated, by providing long range individual molecular context, one can also derive the phasing information of variants within that individual molecular context, e.g., variants on a particular long molecule will be, by definition commonly phased.

By providing longer range individual molecular context, the methods and systems of the invention also provide much longer inferred molecular context (also referred to herein as a "long virtual single molecule read"). Sequence context, as described herein can include mapping or providing linkage of fragments across different (generally on the kilobase scale) ranges of full genomic sequence. These methods include mapping the short sequence reads to the individual longer molecules or contigs of linked molecules, as well as long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

Furthermore, while one may utilize the long range sequence context associated with long individual molecules, having such long range sequence context also allows one to infer even longer range sequence context. By way of one example, by providing the long range molecular context described above, one can identify overlapping variant portions, e.g., phased variants, translocated sequences, etc., among long sequences from different originating molecules, allowing the inferred linkage between those molecules. Such inferred linkages or molecular contexts are referred to herein as "inferred contigs". In some cases when discussed in the context of phased sequences, the inferred contigs may represent commonly phased sequences, e.g., where by virtue of overlapping phased variants, one can infer a phased contig of substantially greater length than the individual originating molecules. These phased contigs are referred to herein as "phase blocks".

By starting with longer single molecule reads (e.g., the "long virtual single molecule reads" discussed above), one can derive longer inferred contigs or phase blocks than would otherwise be attainable using short read sequencing technologies or other approaches to phased sequencing. See, e.g., published U.S. Patent Application No. 2013-0157870. In particular, using the methods and systems described herein, one can obtain inferred contig or phase block lengths having an N50 (where the sum of the block lengths that are greater than the stated N50 number is 50% of the sum of all block lengths) of at least about 10 kb, at least about 20 kb, at least about 50 kb. In more preferred aspects, inferred contig or phase block lengths having an N50 of at least about 100 kb, at least about 150 kb, at least about 200 kb, and in many cases, at least about 250 kb, at least about 300 kb, at least about 350 kb, at least about 400 kb, and in some cases, at least about 500 kb or more, are attained. In still other cases, maximum phase block lengths in excess of 200 kb, in excess of 300 kb, in excess of 400 kb, in excess of 500 kb, in excess of 1 Mb, or even in excess of 2 Mb may be obtained.

In one aspect, and in conjunction with any of the capture methods described above and later herein, the methods and systems described herein provide for the compartmentalization, depositing or partitioning of sample nucleic acids, or fragments thereof, into discrete compartments or partitions (referred to interchangeably herein as partitions), where each partition maintains separation of its own contents from the contents of other partitions. Unique identifiers, e.g., barcodes, may be previously, subsequently or concurrently delivered to the partitions that hold the compartmentalized or partitioned sample nucleic acids, in order to allow for the later attribution of the characteristics, e.g., nucleic acid sequence information, to the sample nucleic acids included within a particular compartment, and particularly to relatively long stretches of contiguous sample nucleic acids that may be originally deposited into the partitions.

The sample nucleic acids utilized in the methods described herein typically represent a number of overlapping portions of the overall sample to be analyzed, e.g., an entire chromosome, exome, or other large genomic portion. These sample nucleic acids may include whole genomes, individual chromosomes, exomes, amplicons, or any of a variety of different nucleic acids of interest. The sample nucleic acids are typically partitioned such that the nucleic acids are present in the partitions in relatively long fragments or stretches of contiguous nucleic acid molecules. Typically, these fragments of the sample nucleic acids may be longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, which permits the longer range molecular context described above.

The sample nucleic acids are also typically partitioned at a level whereby a given partition has a very low probability of including two overlapping fragments of the starting sample nucleic acid. This is typically accomplished by providing the sample nucleic acid at a low input amount and/or concentration during the partitioning process. As a result, in preferred cases, a given partition may include a number of long, but non-overlapping fragments of the starting sample nucleic acids. The sample nucleic acids in the different partitions are then associated with unique identifiers, where for any given partition, nucleic acids contained therein possess the same unique identifier, but where different partitions may include different unique identifiers. Moreover, because the partitioning step allocates the sample components into very small volume partitions or droplets, it will be appreciated that in order to achieve the desired allocation as set forth above, one need not conduct substantial dilution of the sample, as would be required in higher volume processes, e.g., in tubes, or wells of a multiwell plate. Further, because the systems described herein employ such high levels of barcode diversity, one can allocate diverse barcodes among higher numbers of genomic equivalents, as provided above. In particular, previously described, multiwell plate approaches (see, e.g., U.S. Published Application No. 2013-0079231 and 2013-0157870) typically only operate with a hundred to a few hundred different barcode sequences, and employ a limiting dilution process of their sample in order to be able to attribute barcodes to different cells/nucleic acids. As such, they will generally operate with far fewer than 100 cells, which would typically provide a ratio of genomes:(barcode type) on the order of 1:10, and certainly well above 1:100. The systems described herein, on the other hand, because of the high level of barcode diversity, e.g., in excess of 10,000, 100,000, 500,000, 600,000, 700,000 etc. diverse barcode types, can operate at genome:(barcode type) ratios that are on the order of 1:50 or less, 1:100 or less, 1:1000 or less, or even smaller ratios, while also allowing for loading higher numbers of genomes (e.g., on the order of greater than 100 genomes per assay, greater than 500 genomes per assay, 1000 genomes per assay, or even more) while still providing for far improved barcode diversity per genome.

Often, the sample is combined with a set of oligonucleotide tags that are releasably-attached to beads prior to the partitioning step. In some examples, amplification methods are used to add barcodes to the resultant amplification products, which in some examples contain smaller segments (fragments) of the full originating nucleic acid molecule from which they are derived. In some examples, methods using transposons are utilized as described in Amini et al, Nature Genetics 46: 1343-1349 (2014) (advance online publication on Oct. 29, 2014), which is herein incorporated by reference in its entirety for all purposes and in particular for all teachings related to attaching barcodes or other oligonucleotide tags to nucleic acids. In further examples, methods of attaching barcodes can include the use of nicking enzymes or polymerases and/or invasive probes such as recA to produce gaps along double stranded sample nucleic acids—barcodes can then be inserted into those gaps.

In examples in which amplification is used to tag nucleic acid fragments, the oligonucleotide tags may comprise at least a first and second region. The first region may be a barcode region that, as between oligonucleotides within a given partition, may be substantially the same barcode sequence, but as between different partitions, may and, in most cases is a different barcode sequence. The second region may be an N-mer (either a random N-mer or an N-mer designed to target a particular sequence) that can be used to prime the nucleic acids within the sample within the partitions. In some cases, where the N-mer is designed to target a particular sequence, it may be designed to target a particular chromosome (e.g., chromosome 1, 13, 18, or 21), or region of a chromosome, e.g., an exome or other targeted region. As discussed herein, the N-mer may also be designed to selected regions of the genome that tend to be poorly characterized or are highly polymorphic or divergent from the reference sequence. In some cases, the N-mer may be designed to target a particular gene or genetic region, such as a gene or region associated with a disease or disorder (e.g., cancer). Within the partitions, an amplification reaction may be conducted using the second N-mer to prime the nucleic acid sample at different places along the length of the nucleic acid. As a result of the amplification, each partition may contain amplified products of the nucleic acid that are attached to an identical or near-identical barcode, and that may represent overlapping, smaller fragments of the nucleic acids in each partition. The bar-code can serve as a marker that signifies that a set of nucleic acids originated from the same partition, and thus potentially also originated from the same strand of nucleic acid. Following amplification, the nucleic acids may be pooled, sequenced, and aligned using a sequencing algorithm. Because shorter sequence reads may, by virtue of their associated barcode sequences, be aligned and attributed to a single, long fragment of the sample nucleic acid, all of the identified variants on that sequence can be attributed to a single originating fragment and single originating chromosome. Further, by aligning multiple co-located variants across multiple long fragments, one can further characterize that chromosomal contribution. Accordingly, conclusions regarding the phasing of particular genetic variants may then be drawn, as can analyses across long ranges of genomic sequence—for example, identification of sequence information across stretches of poorly characterized regions of the genome. Such information may also be useful for identifying haplotypes, which are generally a specified set of genetic variants that reside on the same nucleic acid strand or on different nucleic acid strands. Copy number variations may also be identified in this manner.

The described methods and systems provide significant advantages over current nucleic acid sequencing technologies and their associated sample preparation methods. Ensemble sample preparation and sequencing methods are predisposed towards primarily identifying and characterizing the majority constituents in the sample, and are not designed to identify and characterize minority constituents, e.g., genetic material contributed by one chromosome, from a poorly characterized or highly polymorphic region of the genome, or material from one or a few cells, or fragmented tumor cell DNA molecule circulating in the bloodstream, that constitute a small percentage of the total DNA in the extracted sample. The methods described herein include selective amplification methods that increase the genetic material from these minority constituents, and the ability to retain the molecular context of this genetic material further provides genetic characterization of these constituents. The described methods and systems also provide a significant advantage for detecting populations that are present within a larger sample. As such, they are particularly useful for assessing haplotype and copy number variations—the methods disclosed herein are also useful for providing sequence information over regions of the genome that are poorly characterized or are poorly represented in a population of nucleic acid targets due to biases introduced during sample preparation.

The use of the barcoding technique disclosed herein confers the unique capability of providing individual molecular context for a given set of genetic markers, i.e., attributing a given set of genetic markers (as opposed to a single marker) to individual sample nucleic acid molecules, and through variant coordinated assembly, to provide a broader or even longer range inferred individual molecular context, among multiple sample nucleic acid molecules, and/or to a specific chromosome. These genetic markers may include specific genetic loci, e.g., variants, such as SNPs, or they may include short sequences. Furthermore, the use of barcoding confers the additional advantages of facilitating the ability to discriminate between minority constituents and majority constituents of the total nucleic acid population extracted from the sample, e.g. for detection and characterization of circulating tumor DNA in the bloodstream, and also reduces or eliminates amplification bias during optional amplification steps. In addition, implementation in a microfluidics format confers the ability to work with extremely small sample volumes and low input quantities of DNA, as well as the ability to rapidly process large numbers of sample partitions (droplets) to facilitate genome-wide tagging.

As noted above, the methods and systems described herein provide individual molecular context for short sequence reads of longer nucleic acids. As used herein, individual molecular context refers to sequence context beyond the specific sequence read, e.g., relation to adjacent or proximal sequences, that are not included within the sequence read itself, and as such, will typically be such that they would not be included in whole or in part in a short sequence read, e.g., a read of about 150 bases, or about 300 bases for paired reads. In particularly preferred aspects, the methods and systems provide long range sequence context for short sequence reads. Such long range context includes relationship or linkage of a given sequence read to sequence reads that are within a distance of each other of longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb, or longer. By providing longer range individual molecular context, the methods and systems of the invention also provide much longer inferred molecular context. Sequence context, as described herein can include lower resolution context, e.g., from mapping the short sequence reads to the individual longer molecules or contigs of linked molecules, as well as the higher resolution sequence context, e.g., from long range sequencing of large portions of the longer individual molecules, e.g., having contiguous determined sequences of individual molecules where such determined sequences are longer than 1 kb, longer than 5 kb, longer than 10 kb, longer than 15 kb, longer than 20 kb, longer than 30 kb, longer than 40 kb, longer than 50 kb, longer than 60 kb, longer than 70 kb, longer than 80 kb, longer than 90 kb or even longer than 100 kb. As with sequence context, the attribution of short sequences to longer nucleic acids, e.g., both individual long nucleic acid molecules or collections of linked nucleic acid molecules or contigs, may include both mapping of short sequences against longer nucleic acid stretches to provide high level sequence context, as well as providing assembled sequences from the short sequences through these longer nucleic acids.

IV. Samples

As will be appreciated, the methods and systems discussed herein can be used to obtain targeted sequence information from any type of genomic material. Such genomic material may be obtained from a sample taken from a patient. Exemplary samples and types of genomic material of use in the methods and systems discussed herein include without limitation polynucleotides, nucleic acids, oligonucleotides, circulating cell-free nucleic acid, circulating tumor cell (CTC), nucleic acid fragments, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like. In summary, the samples that are used may vary depending on the particular processing needs.

Any substance that comprises nucleic acid may be the source of a sample. The substance may be a fluid, e.g., a biological fluid. A fluidic substance may include, but not limited to, blood, cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. The substance may be solid, for example, a biological tissue. The substance may comprise normal healthy tissues, diseased tissues, or a mix of healthy and diseased tissues. In some cases, the substance may comprise tumors. Tumors may be benign (non-cancer) or malignant (cancer). Non-limiting examples of tumors may include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof. The substance may be associated with various types of organs. Non-limiting examples of organs may include brain, liver, lung, kidney, prostate, ovary, spleen, lymph node (including tonsil), thyroid, pancreas, heart, skeletal muscle, intestine, larynx, esophagus, stomach, or combinations thereof. In some cases, the substance may comprise a variety of cells, including but not limited to: eukaryotic cells, prokaryotic cells, fungi cells, heart cells, lung cells, kidney cells, liver cells, pancreas cells, reproductive cells, stem cells, induced pluripotent stem cells, gastrointestinal cells, blood cells, cancer cells, bacterial cells, bacterial cells isolated from a human microbiome sample, etc. In some cases, the substance may comprise contents of a cell, such as, for example, the contents of a single cell or the contents of multiple cells. Methods and systems for analyzing individual cells are provided in, e.g., U.S. patent application Ser. No. 14/752,641, filed Jun. 26, 2015, the full disclosure of which is hereby incorporated by reference in its entirety.

Samples may be obtained from various subjects. A subject may be a living subject or a dead subject. Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. In some cases, the subject may be a patient who is having, suspected of having, or at a risk of developing a disease or disorder. In some cases, the subject may be a pregnant woman. In some case, the subject may be a normal healthy pregnant woman. In some cases, the subject may be a pregnant woman who is at a risking of carrying a baby with certain birth defect.

A sample may be obtained from a subject by any means known in the art. For example, a sample may be obtained from a subject through accessing the circulatory system (e.g., intravenously or intra-arterially via a syringe or other apparatus), collecting a secreted biological sample (e.g., saliva, sputum urine, feces, etc.), surgically (e.g., biopsy) acquiring a biological sample (e.g., intra-operative samples, post-surgical samples, etc.), swabbing (e.g., buccal swab, oropharyngeal swab), or pipetting.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example: Targeted Coverage of TP53 Gene

An amplification reaction targeting the TP53 gene was conducted. Tumor protein p53, also known as p53, cellular tumor antigen p53 (UniProt name), phosphoprotein p53, tumor suppressor p53, antigen NY-CO-13, or transformation-related protein 53 (TRP53), is a protein that is encoded by the TP53 gene in humans. The p53 protein is crucial in multicellular organisms, where it regulates the cell cycle and, thus, functions as a tumor suppressor, preventing cancer. As such, p53 has been described as "the guardian of the genome" because of its role in conserving stability by preventing genome mutation. Hence TP53 is classified as a tumor suppressor gene.

Targeted amplification of the region of the genome containing the TP53 gene (which is about 19149 by in length) was conducted using a total of 96 primers spanning the entire gene in a multiplex reaction. The primers were designed to tile across this region of the genome about 400 by apart. The amplification reaction was conducted with a temperature gradient for the annealing step, 14 cycles, and an input amount of about 3 ng of DNA. The thermocycling protocol used for this example was as follows:

| Initial Denaturation | 98° C. | 30 seconds |
|---|---|---|
| 18 Cycles | 98° C. | 10 seconds |
| | 30-55° C. | 15 seconds |
| | 72° C. | 15 seconds |
| Final Extension | 72° C. | 2 minutes |
| Hold | 4 C | |

Figure 8:
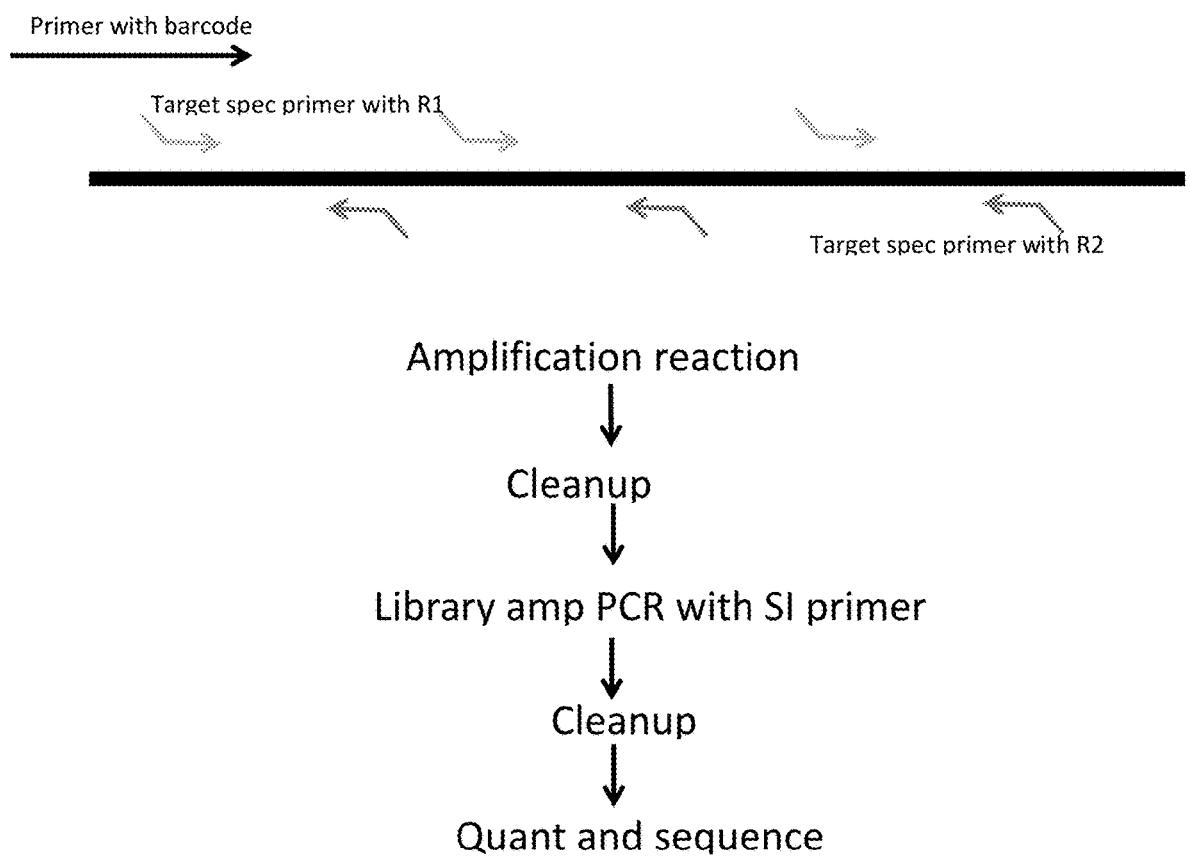
FIG. 8 provides a schematic illustration of an embodiment of the invention.

An exemplary workflow for this type of reaction is pictured in FIG. 8. As will be appreciated, this is an exemplary embodiment of a method in accordance with the invention described herein and can be altered or expanded using known methods. As shown in FIG. 8, the selected region of the genome (in this case, the TP53 gene) is amplified using target specific primers, such as those pictured as 802 and 803. In addition, a primer with barcode 801 was also incorporated into the amplicons, which can in certain embodiments as described herein provide molecular context for the subsequent sequence reads (808).

The primers 802 and 803 had in this experiment "tails" R1 and R2, which rendered the resultant amplicons amenable to sequencing on specific platforms, such as the Illumina platform. The amplification with the SI primer (806) further provided a sample index that is also used with the Illumina platform. As will be appreciated, sequences that are useful for other sequencing platforms can be used in place of the R1 and R2 and S1 primers.

Figure 9:
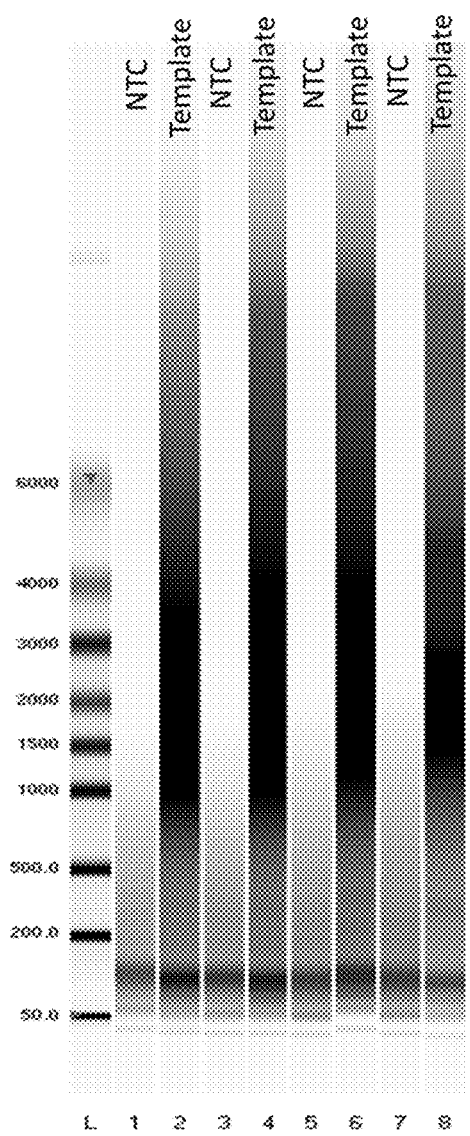
FIG. 9 shows data from an experiment comparing amplification reactions conducted with template compared with those containing no template (NTC).
Figure 10:
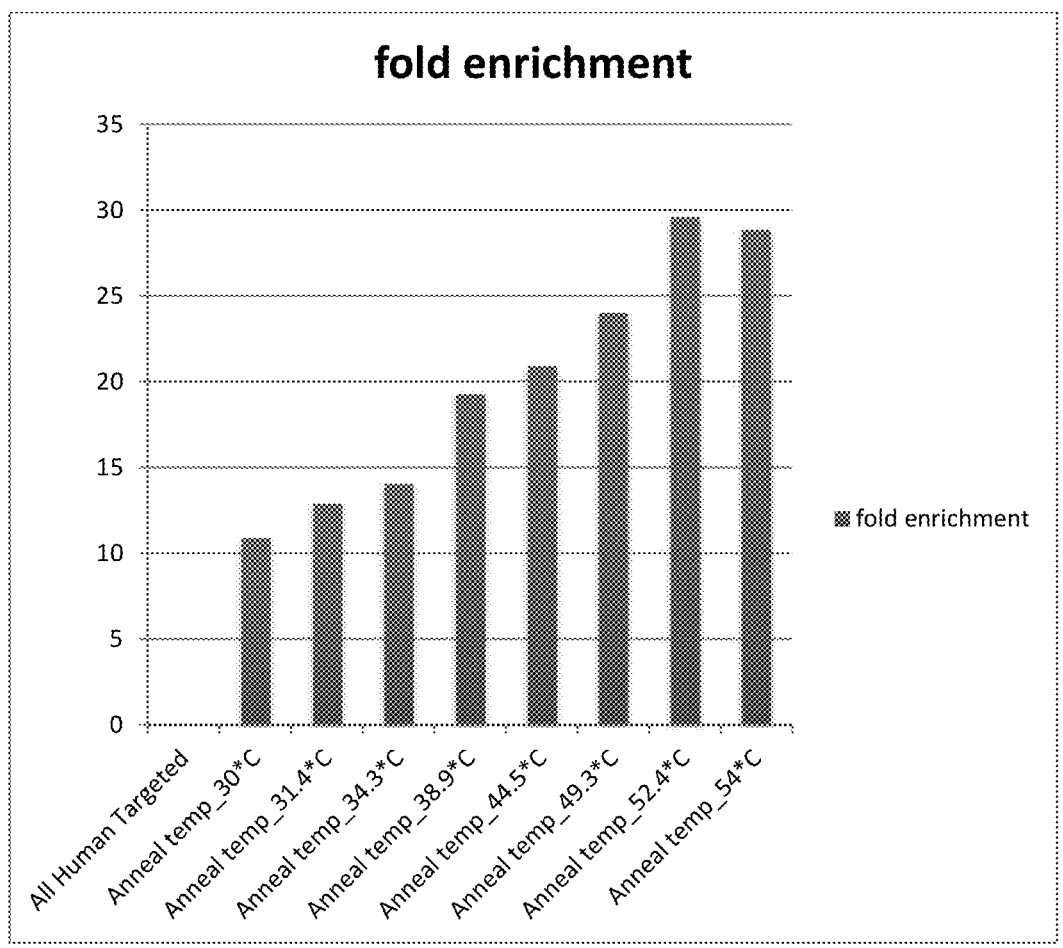
FIG. 10 shows data from amplification reactions conducted across a range of annealing temperatures.

FIG. 9 shows that the amplification reaction was specific, as the no template controls (NTC) showed no product. FIG. 10 provides the fold-enrichment seen as a result of the above-described protocol across a range of temperatures.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed is:

1. A method for sequencing one or more targeted portions of a genome, the method comprising:
    (a) providing starting genomic material;
    (b) distributing individual nucleic acid molecules from the starting genomic material into discrete partitions such that each discrete partition contains an individual nucleic acid molecule;
    (c) amplifying targeted portions of at least some of the individual nucleic acid molecules in the discrete partitions with target specific primers to form a population of amplicons, wherein the targeted portions are one or more regions of an exome or one or more regions of a gene of interest, wherein the amplifying comprises PCR amplification across a single genomic region of at least 3.5 megabase pairs (Mbp) in length;
    (d) barcoding the population of amplicons to form a plurality of barcoded fragments of the amplicons, wherein fragments within a given discrete partition each comprise a common barcode, thereby associating each fragment with the individual nucleic acid molecule from which it is derived;
    (e) obtaining sequence information from the plurality of fragments thereby sequencing one or more targeted portions of a genome.

2. The method of claim 1, wherein the one or more targeted portions of the genome comprise highly polymorphic regions of the genome.

3. The method of claim 1, wherein the sequencing of the one or more targeted portions of the genome is a de-novo sequencing.

4. The method of claim 1, wherein the amplifying comprises a PCR amplification utilizing multiple primer pairs staggered across a region of at least 3.0 megabase pairs (Mbp).

5. The method of claim 4, wherein the multiple primer pairs contain uracils to prevent amplification of the primer sequences.

6. The method of claim 1, wherein the obtaining step (e) comprises a sequencing reaction selected from the group consisting of: short read-length sequencing reactions and long read-length sequencing reactions.

7. The method of claim 6, wherein the sequencing reaction is a short read, high accuracy sequencing reaction.

8. The method of claim 1, wherein the sequence information generated in obtaining step (e) retains the molecular context of its originating individual nucleic acid.

9. The method of claim 1, wherein prior to the obtaining step (e), the plurality of fragments is further enriched for fragments comprising at least a portion of the one or more targeted portions of the genome by:
    (i) hybridizing probes complementary to regions in or near the one or more targeted portions of the genome to the fragments to form probe-fragment complexes;
    (ii) capturing probe-fragment complexes to a surface of a solid support.

10. The method of claim 9, wherein the solid support comprises a bead.

11. The method of claim 1, wherein the method further comprises linking two or more of the individual nucleic acid molecules in an inferred contig based upon overlapping sequences of the plurality of fragments, wherein the inferred contig comprises a length N50 of at least 10 kb.

12. The method of claim 11, wherein the inferred contig comprises a length N50 of at least 20 kb.

13. The method of claim 11, wherein the inferred contig comprises a length N50 of at least 40 kb.

14. The method of claim 11, wherein the inferred contig comprises a length N50 of at least 50 kb.

15. The method of claim 11, wherein the inferred contig comprises a length N50 of at least 100 kb.

16. The method of claim 11, wherein the inferred contig comprises a length N50 of at least 200 kb.

17. The method of claim 1, wherein the barcode of the barcoded fragments further comprises additional sequence segments.

18. The method of claim 17, wherein the additional sequence segments comprise one or more of a member selected from the group consisting of: primers, attachment sequences, random n-mer oligonucleotides, oligonucleotides comprising uracil nucleobases.

19. The method of claim 1, wherein the barcoding comprises attaching a barcode selected from a library of at least 700,000 barcodes.

20. The method of claim 1, wherein the barcoded fragments of the amplicons within the discrete partitions represent about 100×-5000× coverage of the one or more selected portions of the genome.

21. The method of claim 1, wherein the barcoded fragments of the amplicons within the discrete partitions represent about 200×-1000× coverage of the one or more selected portions of the genome.

22. The method of claim 1, wherein the barcoded fragments of the amplicons within the discrete partitions represent at least 1000× coverage of the one or more selected portions of the genome.

23. The method of claim 1, wherein the barcoded fragments of the amplicons within the discrete partitions represent at least 2000× coverage of the one or more selected portions of the genome.

24. The method of claim 1, wherein the barcoded fragments of the amplicons within the discrete partitions represent at least 5000× coverage of the one or more targeted portions of the genome.

25. A method for obtaining sequence information from one or more targeted portions of a genomic sample while retaining molecular context, the method comprising (a) providing starting genomic material;
(b) distributing individual nucleic acid molecules from the starting genomic material into discrete partitions such that each discrete partition contains a first individual nucleic acid molecule;
(c) providing a population enriched for fragments comprising at least a portion of the one or more targeted portions of the genomic sample by amplification of the sample using target specific primers, wherein the targeted portions are one or more regions of an exome or one or more regions of a gene of interest, wherein the amplification comprises PCR amplification across a single genomic region of at least 3.5 megabase pairs (Mbp) in length;
(d) attaching a common barcode sequence to the fragments within each discrete partition such that each of the fragments is attributable to the discrete partition in which it was contained;
(e) obtaining sequence information from the fragments, thereby sequencing one or more targeted portions of the genomic sample while retaining molecular context.

26. The method of claim 1, wherein one or more of the discrete partitions each contain multiple individual nucleic acid molecules.

* * * * *